US012648996B2

(12) United States Patent
Serafini et al.

(10) Patent No.: US 12,648,996 B2
(45) Date of Patent: Jun. 9, 2026

(54) RNA APTAMERS AND USES THEREOF

(71) Applicants: UNIVERSITY OF MIAMI, Miami, FL (US); University of Verona, Verona (IT); UNIVERSITY OF MODENA AND REGGIO EMILIA—UNIMORE, Modena (IT)

(72) Inventors: Paolo Serafini, Miami Shores, FL (US); Silvio Bicciato, Modena (IT); Jimmy Caroli, Modena (IT); Adriana De La Fuente, Miami, FL (US); Dimitri Van Simaeys, Miami Beach, FL (US); Serena Zilio, Miami, FL (US); Vincenzo Bronte, Verona (IT)

(73) Assignee: UNIVERSITY OF MIAMI, Miami, FL (US)

( * ) Notice: Subject to any disclaimer, the term of this patent is extended or adjusted under 35 U.S.C. 154(b) by 907 days.

(21) Appl. No.: 17/436,773

(22) PCT Filed: Mar. 3, 2020

(86) PCT No.: PCT/US2020/020799
§ 371 (c)(1),
(2) Date: Sep. 7, 2021

(87) PCT Pub. No.: WO2020/180868
PCT Pub. Date: Sep. 10, 2020

(65) Prior Publication Data
US 2022/0175935 A1    Jun. 9, 2022

Related U.S. Application Data

(60) Provisional application No. 62/815,142, filed on Mar. 7, 2019.

(51) Int. Cl.
A61K 47/54        (2017.01)
A61K 31/704       (2006.01)
(Continued)

(52) U.S. Cl.
CPC .......... *A61K 47/549* (2017.08); *A61K 31/704* (2013.01); *A61K 31/7105* (2013.01); *A61K 31/711* (2013.01); *A61P 35/00* (2018.01)

(58) Field of Classification Search
CPC ................ A61K 47/549; A61K 31/704; A61K 31/7105; A61K 31/711; A61P 35/00;
(Continued)

(56) References Cited

U.S. PATENT DOCUMENTS

2013/0266515 A1    10/2013  Duconge et al.
2016/0003835 A1*    1/2016  Halbert .............. G01N 33/5308
506/9

FOREIGN PATENT DOCUMENTS

WO      WO-2017/173247 A1    10/2017

OTHER PUBLICATIONS

Bagalkot, V., Farokhzad, O.C., Langer, R. and Jon, S. (2006), An Aptamer-Doxorubicin Physical Conjugate as a Novel Targeted Drug-Delivery Platform. Angewandte Chemie International Edition, 45: 8149-8152. (Year: 2006).*
(Continued)

*Primary Examiner* — Brian Whiteman
*Assistant Examiner* — Amanda M Zahorik
(74) *Attorney, Agent, or Firm* — MARSHALL, GERSTEIN & BORUN LLP

(57)        ABSTRACT
Described herein and RNA aptamers that specifically bind to tumor-infiltrating myeloid cells and uses thereof.

5 Claims, 14 Drawing Sheets

Specification includes a Sequence Listing.

(51) Int. Cl.
    *A61K 31/7105*        (2006.01)
    *A61K 31/711*         (2006.01)
    *A61P 35/00*          (2006.01)
(58) Field of Classification Search
    CPC .............. C12N 2310/16; C12N 15/115; G01N
                              33/5091; G01N 33/57407
    See application file for complete search history.

(56)                    References Cited

OTHER PUBLICATIONS

McNamara, J., Andrechek, E., Wang, Y. et al. Cell type-specific delivery of siRNAs with aptamer-siRNA chimeras. Nat Biotechnol 24, 1005-015 (2006). (Year: 2006).*
Cibiel A, Nguyen Quang N, Gombert K, Theze B, Garofalakis A, Duconge F (2014) From Ugly Duckling to Swan: Unexpected Identification from Cell-SELEX of an Anti-Annexin A2 Aptamer Targeting Tumors. PLoS ONE 9(1): e87002. (Year: 2014).*
Wengerter BC, Katakowski JA, Rosenberg JM, Park CG, Almo SC, Palliser D, Levy M. Aptamer-targeted antigen delivery. Mol Ther. Jul. 2014;22(7):1375-1387. (Year: 2014).*
Moss SE, Morgan RO. The annexins. Genome Biol. 2004;5(4):219. (Year: 2004).*
Rehman S, Rahimi N, Dimri M. Biochemistry, G Protein Coupled Receptors. [Updated Jul. 30, 2023]. In: StatPearls [Internet]. Treasure Island (FL): StatPearls Publishing; Jan. 2024. Available from: https://www.ncbi.nlm.nih.gov/books/NBK518966/ (Year: 2023).*
Takahashi M. Nucleic Acid Aptamers Emerging as Modulators of G-Protein-Coupled Receptors: Challenge to Difficult Cell Surface Proteins. Cells. Jun. 2, 2022;11(11):1825. (Year: 2022).*
Sun J, Wei Q, Zhou Y, Wang J, Liu Q, Xu H. A systematic analysis of FDA-approved anticancer drugs. BMC Syst Biol. Oct. 3, 2017; 11(Suppl 5):87. doi: 10.1186/s12918-017-0464-7. (Year: 2017).*
Wang et al. Front. Immunol., Aug. 26, 2019 Sec. Molecular Innate Immunity vol. 10—2019 (Year: 2019).*
Guizhi Zhu, Xiaoyuan Chen, Aptamer-based targeted therapy, Advanced Drug Delivery Reviews, vol. 134,2018,pp. 65-78, ISSN 0169-409X. (Year: 2018).*
Technology Networks. All Cancers, Great and Small. Cancer Research From Technology Networks, Oct. 13, 2021, www.technologynetworks.com/cancer-research/articles/all-cancers-great-and-small-354029. (Year: 2021).*
Krzyszczyk P et al. The growing role of precision and personalized medicine for cancer treatment. Technology (Singap World Sci). Sep.-Dec. 2018;6(3-4):79-100. (Year: 2018).*
Elliott et al., Human tumor-infiltrating myeloid cells: phenotypic and functional diverstiy, Frontiers in Immunol., 8: 86, (Feb. 2017).
Xiang et al., Nucleic acid aptamer-guided cancer therapeutics and diagnostics: the next generation of cancer medicine, Theranostics, 5(1): 23-42, (2015).
"Abstract PR16: RNA Aptamers Specific for Tumor-Infilrating Myeloid Cells," Cancer Immunology Reseach, 8(4) (2018).
Achyut et al., "Myeloid cell signatures in tumor microenvironment predicts therapeutic response in cancer," OncoTargets and therapy 9, 1047-1055 (2016).
Ahmed et al., Radiofrequency thermal ablation sharply increases intratumoral liposomal doxorubicin accumulation and tumor coagulation. Cancer Res 63, 6327-6333 (2003).
Al-Khami et al., "Exogenous lipid uptake induces metabolic and functional reprogramming of tumor-associated myeloid-derived suppressor cells," Oncolmmunology 6, e1344804 (2017).
Alizadeh et al., "Doxorubicin eliminates myeloid-derived suppressor cells and enhances the efficacy of adoptive T-cell transfer in breast cancer," Cancer Res 74, 104-118 (2014).
Ansari et al., "The most prevalent side effects of pegylated liposomal doxorubicin monotherapy in women with metastatic breast cancer: a systematic review of clinical trials," Cancer gene therapy 24, 189-193 (2017).

Apolloni et al., "Immortalized myeloid suppressor cells trigger apoptosis in antigen-activated T lymphocytes," J Immunol 165, 6723-6730 (2000).
Arina et al., "Enhancing T cell therapy by overcoming the immunosuppressive tumor microenvironment," Semin Immunol, (2016).
Aslakson et al., "Selective events in the metastatic process defined by analysis of the sequential dissemination of subpopulations of a mouse mammary tumor," Cancer Res 52, 1399-1405 (1992).
Attarwala, "Role of antibodies in cancer targeting," Journal of Natural Science, Biology, and Medicine 1, 53-56 (2010).
Bagalkot et al., "An aptamer-doxorubicin physical conjugate as a novel targeted drug-delivery platform," Angew Chem Int Ed Engl 45, 8149-8152 (2006).
Bahrami et al., "Nanoparticles and targeted drug delivery in cancer therapy," Immunology letters 190, 64-83 (2017).
Barth et al., "Unique murine tumor-associated antigens identified by tumor infiltrating lymphocytes," The Journal of Immunology 144, 1531-1537 (1990).
Belyaev et al., "Daunorubicin conjugated with alpha-fetoprotein selectively eliminates myeloid-derived suppressor cells (MDSCs) and inhibits experimental tumor growth," Cancer immunology, immunotherapy : CII 67, 101-111 (2018).
Benes et al., "Role of vimentin in regulation of monocyte/macrophage differentiation," Differentiation 74, 265-276 (2006).
Bilalic et al., "Lymphocyte activation induces cell surface expression of an immunogenic vimentin isoform," Transplant immunology 27, 101-106 (2012).
Boye et al., "Annexin A4 and A6 induce membrane curvature and constriction during cell membrane repair," Nature Communications 8, 1623 (2017).
Brattain et al., "Establishment of mouse colonic carcinoma cell lines with different metastatic properties," Cancer Res 40, 2142-2146 (1980).
Bulbake et al., "Liposomal Formulations in Clinical Use: An Updated Review," Pharmaceutics 9, 12 (2017).
Caron et al., "APTANI: a computational tool to select aptamers through sequence-structure motif analysis of HT-SELEX data," Bioinformatics 32, 161-164 (2016).
Carvalho et al., "Doxorubicin: The good, the bad and the ugly effect," Current medicinal chemistry 16, 3267-3285 (2009).
Catuogno et al., "Aptamer Cell-Based Selection: Overview and Advances," Biomedicines 5(49), (2017).
Condamine et al., "Regulation of tumor metastasis by myeloid-derived suppressor cells," Annu Rev Med 66, 97-110 (2015).
De al Fuente et al., "RNA Aptamers Specific for Tumor-Inflitrating Myeloid Cells," Proceedings of the AACR Speciakl Conference on Tumor Immunology and Immunotherapy (Nov. 30, 2018).
Desclaux et al., "A novel and efficient gene transfer strategy reduces glial reactivity and improves neuronal survival and axonal growth in vitro," PLoS One 4, e6227 (2009).
Diakonova et al., "Localization of five annexins in J774 macrophages and on isolated phagosomes," Journal of Cell Science 110, 1199-1213 (1997).
Erez et al., "Leukocytes as paracrine regulators of metastasis and determinants of organ-specific colonization," Int J Cancer 128, 2536-2544 (2011).
First Office Action for Chinese Application 202080034008.3, dated Aug. 10, 2023.
Fleming et al., "Targeting Myeloid-Derived Suppressor Cells to Bypass Tumor-Induced Immunosuppression," Frontiers in immunology 9, 398 (2018).
Gallina et al., "Tumors induce a subset of inflammatory monocytes with immunosuppressive activity on CD8+ T cells," J Clin Invest 116, 2777-2790 (2006).
Hamada et al., "Novel therapeutic strategies targeting tumor-stromal interactions in pancreatic cancer," Frontiers in physiology 4, 331 (2013).
Hamada, "In silico approaches to RNA aptamer design," Biochimie, 145:8-14 (2017).
International Search Report and Written Opinion for Application No. PCT/US2020/020799, dated Jun. 12, 2020.
Kelderman et al., "Acquired and intrinsic resistance in cancer immunotherapy," Molecular Oncology 8, 1132-1139 (2014).

(56)        References Cited

OTHER PUBLICATIONS

Kinnear et al., "Form Follows Function: Nanoparticle Shape and Its Implications for Nanomedicine," Chemical reviews 117, 11476-11521 (2017).

Kitamura et al., "Immune cell promotion of metastasis," Nat Rev Immunol., 15, 73-86 (2015).

Kumar et al., "The nature of myeloid-derived suppressor cells in the tumor microenvironment," Trends in immunology 37, 208-220 (2016).

Kusmartsev et al., "Tumor-associated CD8+ T cell tolerance induced by bone marrow-derived immature myeloid cells," J Immunol 175, 4583-4592 (2005).

Kusmartsev et al., "STAT1 signaling regulates tumor-associated macrophage-mediated T cell deletion," J Immunol 174, 4880-4891 (2005).

Kydd et al., "Targeting Strategies for the Combination Treatment of Cancer Using Drug Delivery Systems," Pharmaceutics 9(46), (2017).

Layzer et al., "Simultaneous generation of aptamers to multiple gamma-carboxyglutamic acid proteins from a focused aptamer library using DeSELEX and convergent selection," Oligonucleotides 17, 1-11 (2007).

Liu et al., "A Novel DNA Aptamer for Dual Targeting of Polymorphonuclear Myeloid-Derived Suppressor Cells and Tumor Cells," Theranostics, 8(1):34-44 (2018).

Lou et al., "Epithelial-mesenchymal transition (EMT) is not sufficient for spontaneous murine breast cancer metastasis," Dev Dyn 237, 2755-2768 (2008).

Martinez et al., "Genetic programs expressed in resting and IL-4 alternatively activated mouse and human macrophages: similarities and differences," Blood 121, e57-e69 (2013).

Marvel et al., "Myeloid-derived suppressor cells in the tumor microenvironment: expect the unexpected," J Clin Invest 125, 3356-3364 (2015).

Mitra et al., "Cell-surface Vimentin: A mislocalized protein for isolating csVimentin(+) CD133(−) novel stem-like hepatocellular carcinoma cells expressing EMT markers," International journal of cancer 137, 491-496 (2015).

Mor-Vaknin et al., "Vimentin is secreted by activated macrophages," Nat Cell Biol 5, 59-63 (2003).

Murphy et al., "A murine renal cell carcinoma," Journal of the National Cancer Institute 50, 1013-1025 (1973).

Nanni et al., "TS/A: a new metastasizing cell line from a BALB/c spontaneous mammary adenocarcinoma," Clinical & experimental metastasis 1, 373-380 (1983).

Pollard, "Tumour-educated macrophages promote tumour progression and metastasis," Nat Rev Cancer 4, 71-78 (2004).

Prabhakar et al., "Challenges and key considerations of the enhanced permeability and retention (EPR) effect for nanomedicine drug delivery in oncology," Cancer research 73, 2412-2417 (2013).

Pulaski et al., "Mouse 4T1 breast tumor model," Current protocols in immunology Chapter 20, Unit 20.22 (2001).

Qin et al., "Generation of a new therapeutic peptide that depletes myeloid-derived suppressor cells in tumor-bearing mice," Nature medicine 20, 676-681 (2014).

Rafiyath et al., "Comparison of safety and toxicity of liposomal doxorubicin vs. conventional anthracyclines: a meta-analysis," Experimental Hematology & Oncology 1, 10 (2012).

Roth et al., "Aptamer-Mediated Blockage of IL4Ra Triggers Apoptosis of MDSCs and Limits Tumor Progression," Cancer Res., 72(6):1373-1383.

Ruella et al., "Treatment of leukemia antigen-loss relapses occurring after CD19-targeted immunotherapies by combination of anti-CD123 and anti-CD19 chimeric antigen receptor T cells," Journal for Immunotherapy of Cancer 3, O5-O5 (2015).

Sarkar et al., "GD3 synthase regulates epithelial-mesenchymal transition and metastasis in breast cancer," Oncogene 34, 2958-2967 (2015).

Serafini et al., "Phosphodiesterase-5 inhibition augments endogenous antitumor immunity by reducing myeloid-derived suppressor cell function," J Exp Med 203, 2691-2702 (2006).

Serafini, "Myeloid derived suppressor cells in physiological and pathological conditions: the good, the bad, and the ugly," Immunol Res 57, 172-184 (2013).

Sica et al., "Altered macrophage differentiation and immune dysfunction in tumor development," J Clin Invest 117, 1155-1166 (2007).

Steidl et al., "Tumor-associated macrophages and survival in classic Hodgkin's lymphoma," N Engl J Med 362, 875-885 (2010).

Stuart et al., "Site-Specific DNA-Doxorubicin Conjugates Display Enhanced Cytotoxicity to Breast Cancer Cells," Bioconjugate Chemistry 25, 406-413 (2014).

Szot et al., "Tumor stroma-targeted antibody-drug conjugate triggers localized anticancer drug release," The Journal of Clinical Investigation 128, 2927-2943 (2018).

Tiet et al., "Exploiting homing abilities of cell carriers: Targeted delivery of nanoparticles for cancer therapy," Biochemical pharmacology, (2017).

Ugel et al., "Tumor-induced myeloid deviation: when myeloid-derived suppressor cells meet tumor-associated macrophages," J Clin Invest 125, 3365-3376 (2015).

Veglia et al., "Myeloid-derived suppressor cells coming of age," Nat Immunol 19, 108-119 (2018).

Weed et al., "Tadalafil reduces myeloid-derived suppressor cells and regulatory T cells and promotes tumor immunity in patients with head and neck squamous cell carcinoma," Clin Cancer Res 21, 39-48 (2015).

Williams et al., "A Proinflammatory Role for Proteolytically Cleaved Annexin A1 in Neutrophil Transendothelial Migration," J. Immunol., 185(5):3057-3063 (Sep. 1, 2010).

Youn et al., "Epigenetic silencing of retinoblastoma gene regulates pathologic differentiation of myeloid cells in cancer," Nature immunology 14, 211-220 (2013).

Zhang et al., "CC chemokine ligand 2 (CCL2) promotes prostate cancer tumorigenesis and metastasis," Cytokine Growth Factor Rev 21, 41-48 (2010).

Zhou et al., "Aptamers as targeted therapeutics: current potential and challenges," Nature reviews. Drug discovery 16, 181-202 (2017).

Zilio et al., "4PD Functionalized Dendrimers: A Flexible Tool for In Vivo Gene Silencing of Tumor-Educated Myeloid Cells," J Immunol 198, 4166-4177 (2017).

Zilio et al., "Neutrophils and Granulocytic MDSC: The Janus God of Cancer Immunotherapy," Vaccines 4, (2016).

\* cited by examiner

6

14

3

11

| Apt. | Kd vs IL4+MSC2 | Putative target | Mascot mass score | % of target covered | Kd vs target |
|------|------|------|------|------|------|
| # 3 | $8.8 \times 10^{-8}$ | ANX IV | 652 | 37.36% | $5.5 \times 10^{-7}$ |
| # 6 | $8.8 \times 10^{-8}$ | N/A | | | |
| # 11 | $3.4 \times 10^{-7}$ | VIM | 1589 | 67.52% | $7.7 \times 10^{-7}$ |
| # 14 | $1.9 \times 10^{-7}$ | N/A | | | | irr apt vs ANXA4
apt 3 vs CTRL prot
apt 3 vs ANXA4 irr apt vs VIM
apt 11 vs CTRL prot
apt 11 vs VIMV

Apt# 3 (50 pMoles)

p<0.001

CTRL    150 pMoles / 500 pMoles Recombinant ANXA4    500 pMoles BSA

Apt#11 (50pMoles)

p<0.001

CTRL    VIM siRNA    scrambled siRNA

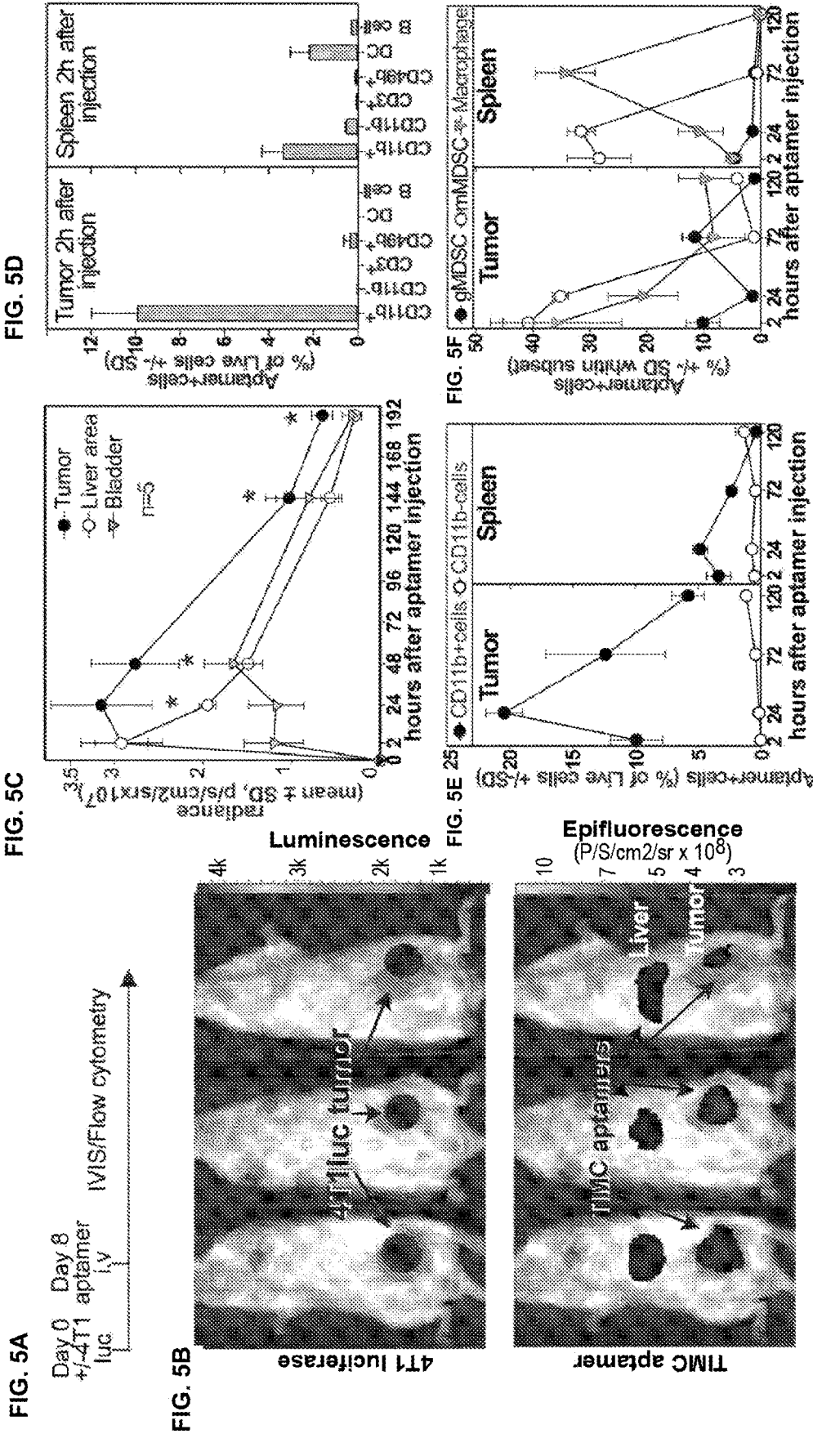

aptamers/dox conjugates

MDSC aptamer

SEQ ID NO: 53

GC-rich tail

Dox

~6.2 dox/apt

| Group | n | multiple comparison Holm-Sidak method |
|---|---|---|
| No treatment | 21 | p=5×10⁻⁸ |
| TIMC-APT/dox (0.35 mg/kg) | 20 | p=2×10⁻⁴ |
| Free Dox (3.5 mg/kg) | 18 | |
| Doxil (0.35 mg/kg) | 8 | p=2×10⁻⁵ |
| Free Dox (0.35 mg/kg) | 6 | p=8×10⁻⁶ |
| CTRL-APT/dox (0.35 mg/kg) | 10 | p=4×10⁻⁷ |
| TIMC-APT | 10 | p=2×10⁻⁷ |

FIG. 10

| SEQ ID NO | # | Aptamer sequence | Apt. frequency (%) | Motif (SEQ ID NO) | Motif frequency (%) |
|---|---|---|---|---|---|
| 1 | 1 | 5'GGAGGACGAUGCGGCCUAGUACACAAGAUC UGACACCUCGAUACAGAUAUGAGGCAGACGAC UCGCUGAGGAUCCGAGA3' | 0.06 | ACAGAU<br>GACACCUCGAUAC (SEQ ID NO: 48)<br>GAU ‖ AU | 0.13<br>0.1<br>2.38 |
| 2 | 2 | 5'GGAGGACGAUGCGGCCUAGUACAAAAGCCU GAUCUCUGUGAGCAGACACUAGAACAGACGAC UCGCUGAGGAUCCGAGA3' | 0.06 | GAGCAGAC | 0.29 |
| 3 | 3 | 5'GGAGGACGAUGCGGAUUACCAACUUGAACG CCGAGAGUGUGGUCACGUGUUCUGCAGACGA CUCGCUGAGGAUCCGAGA3' | 0.12 | GAACGCC<br>CCAAC ‖ GAGUG<br>CCAAC ‖ UG | 0.48<br>1.33<br>0.69 |
| 4 | 4 | 5'GGAGGACGAUGCGGCAACAAACUAAUCAGAC ACGAGACAGAGAGAUAGAUCUGACAGACGACU CGCUGAGGAUCCGAGA3' | 0.36 | CAGACACG | 0.14 |
| 5 | 5 | 5'GGAGGACGAUGCGGCCGGAGGCAGUCACUA AUCUUCACUUCUCUCAGACAUGCGCAGACGAC UCGCUGAGGAUCCGAGA3' | 0.34 | CGGAG | 1.8 |
| 6 | 6 | 5'GGAGGACGAUGCGGCAGGUGCGGGAUCUAA UGCGUAGACAGCCAUAUACUGACACAGACGAC UCGCUGAGGAUCCGAGA3' | 0.4 | GC ‖ GAC<br>CGUAGACAG<br>UGCGGGA<br>GCCAUAUAC<br>UAGACAG | 9.5<br>0.18<br>0.11<br>0.1<br>0.1 |
| 7 | 7 | 5'GGAGGACGAUGCGGACGACGUUUACUGACC ACGAUAUGUCAGAUUCGGUCCUCAUCAGACGA CUCGCUGAGGAUCCGAGA3' | 0.05 | CCACGAUAUG (SEQ ID NO: 49) | 0.54 |
| 8 | 8 | 5'GGAGGACGAUGCGGCAUACACACUUGACUC UAGAGAACGAGCAUCUAGCGGUGUCCAGACGA CUCGCUGAGGAUCCGAGA3' | 0.07 | AUACACACUU (SEQ ID NO: 50)<br>CUAGAGAACG (SEQ ID NO: 51) | 0.11<br>0.3 |
| 9 | 9 | 5'GGAGGACGAUGCGGGUGACUAGGCAAGCAC AAAACUGUCGCUCAUGACAGAUCUGUCAGACG ACUCGCUGAGGAUCCGAGA3' | 0.09 | CGCUCAUG<br>AGAUCU<br>UGACUAGG<br>UAGGCAA<br>AAAACU<br>CA ‖ UCG | 1.57<br>0.26<br>0.15<br>0.12<br>0.1<br>0.57 |
| 10 | 10 | 5'GGAGGACGAUGCGGACGGAGGAUAGUUGCU AAUCGAGCGCUGCCGACGCUCCAGACGACUC GCUGAGGAUCCGAGA3' | 3.61 | GGAG ‖ CGAC<br>GGAGG ‖ CGAGC<br>GAU ‖ GC<br>UUG ‖ CG<br>GGAG ‖ CC | 13.43<br>3.61<br>33.35<br>18.87<br>0.78 |
| 11 | 11 | 5'GGAGGACGAUGCGGGGAAGCAACACUUAGU CGCGAUUGAUACGUGCGCAGUCAUCAGACGAC UCGCUGAGGAUCCGAGA3' | 1.01 | GCAACAC | 1.49 |
| 12 | 12 | 5'GGAGGACGAUGCGGGGAAGCAACACUUAGU CGCGAUUGAUACGUGCGCAGUCAGCAGACGA CUCGCUGAGGAUCCGAGA3' | 0.63 | GAUACGUGCGC (SEQ ID NO: 52) | 0.18 |
| 13 | 13 | 5'GGAGGACGAUGCGGACGGAGGAUAGUUGCU AAUCGAGCGCUGCGCACGCUCCAGACGACUC GCUGAGGAUCCGAGA3' | 0.78 | GUUGC<br>GCUGCGCAC<br>UA ‖ UAA | 1.42<br>0.16<br>4.58 |
| 14 | 14 | 5'GGAGGACGAUGCGGUGUACACUGAUUGCCU UUGUGUUAUGAGCGACAGAUCUGCCAGACGAC UCGCUGAGGAUCCGAGA3' | 0.16 | UAUGAGCG | 0.8 |
| 15 | 15 | 5'GGAGGACGAUGCGGUGUACACUGAUUGCCU CUGUGUUAUGAGCGACAGAUCUGCCAGACGAC UCGCUGAGGAUCCGAGA3' | 0.15 | UUAUGAG<br>UG ‖ CGA | 0.79<br>12.27 |

FIG. 11

| SEQ ID | Sequence | Oligonucleotides |
|---|---|---|
| 16 and 17 | Sullenger library | 5'-TCTCGGATCCTCAGCGAGTCGTCTG (40N) CCGCATCGTCCTCCCTA-3' |
| 18 | SUL3' | 5'-TCTCGGATCCTCAGCGAGTCGTC-3' |
| 19 | SUL5' | 5'-GGGGGAATTCTAATACGACTCACTATAGGGAGGACGATGCGG-3' |
| 20 | SUL3short | 5'- TCTCGGATCCTCAGCGAGTC-3' |
| 21 | GC-rich-SUL3' | 5'-ATC GAT CGA TCG ATC GAT CGA TCG ATC GAT TTT TCG ATC GAT CGA TCG ACT GAT CGA TCG TCTCGGATCCTCAGCGAGTCGTC-3' |
| 22 | Apt#1 oligo | 5'-TAGGGAGGACGATGCGG CCT AGT ACA CAA GAT CTG ACA CCT CGA TAC AGA TAT GAG GCA GACGACTCGCTGAGGATCCGAGA-3' |
| 23 | Apt#2 oligo | 5'-TAGGGAGGACGATGCGG CCT AGT ACA AAA GCC TGA TCT CTG TGA GCA GAC ACT AGA ACA GACGACTCGCTGAGGATCCGAGA-3' |
| 24 | Apt#3 oligo | 5'-TAGGGAGGACGATGCGG ATT ACC AAC TTG AAC GCC GAG AGT GTG GTC ACG TGT TCT GCA GACGACTCGCTGAGGATCCGAGA-3' |
| 25 | Apt#4 oligo | 5'-TAGGGAGGACGATGCGG CAA CAA ACT AAT CAG ACA CGA GAC AGA GAG ATA GAT CTC ACA GACGACTCGCTGAGGATCCGAGA-3' |
| 26 | Apt#5 oligo | 5'-TAGGGAGGACGATGCGG CCG GAG GCA GTC ACT AAT CTT CAC TTC TCT CAG ACA TGC GCA GACGACTCGCTGAGGATCCGAGA-3' |
| 27 | Apt#6 oligo | 5'-TAGGGAGGACGATGCGG CAG GTG CGG GAT CTA ATG CGT AGA CAG CCA TAT ACT GAC ACA GACGACTCGCTGAGGATCCGAGA-3' |
| 28 | Apt#7 oligo | 5'-TAGGGAGGACGATGCGG ACG ACG TTT ACT GAC CAC GAT ATG TCA GAT TCG CTC CTC ATC A GACGACTCGCTGAGGATCCGAGA-3' |
| 29 | Apt#8 oligo | 5'-TAGGGAGGACGATGCGG CAT ACA CAC TTG ACT CTA GAG AAG GAG CAT CTA CCG GTG TCC A GACGACTCGCTGAGGATCCGAGA-3' |
| 30 | Apt#9 oligo | 5'-TAGGGAGGACGATGCGG GTG ACT AGG CAA GCA CAA AAC TGT CGC TCA TGA CAG ATC TGT CA GACGACTCGCTGAGGATCCGAGA-3' |
| 31 | Apt#10 oligo | 5'-TAGGGAGGACGATGCGG ACG GAG GAT AGT TGC TAA TCG AGC GCT GCC GAC GCT CCA GACGACTCGCTGAGGATCCGAGA-3' |
| 32 | Apt#11 oligo | 5'-TAGGGAGGACGATGCGG GGA AGC AAC ACT TAG TCG CGA TTG ATA CGT GCG CAG TCA GACGACTCGCTGAGGATCCGAGA-3' |
| 33 | Apt#12 oligo | 5'-TAGGGAGGACGATGCGG GGA AGC AAC ACT TAG TCG CGA TTG ATA CGT GCG CAG TCA GCA GACGACTCGCTGAGGATCCGAGA-3' |
| 34 | Apt#13 oligo | 5'-TAGGGAGGACGATGCGG ACG GAG GAT AGT TGC TAA TCG AGC GCT GCG CAC GCT CCA GACGACTCGCTGAGGATCCGAGA-3' |
| 35 | Apt#14 oligo | 5'-TAGGGAGGACGATGCGG TGT ACA CTG ATT GCC TTT GTG TTA TGA GCG ACA GAT CTG CCA GACGACTCGCTGAGGATCCGAGA-3' |
| 36 | Apt#15 oligo | 5'-TAGGGAGGACGATGCGG TGT ACA CTG ATT GCC TCT GTG TTA TGA GCG ACA GAT CTG CCA GACGACTCGCTGAGGATCCGAGA-3' |
| | | Illumina oligonucleotide |
| 37 | ILL-PF1 A | ACACTCTTTCCCTACACGACGCTCTTCCGATCTCTAGTGAGGACGATGCGG |
| 38 | ILL-PF2 A | ACACTCTTTCCCTACACGACGCTCTTCCGATCTAGCTGGAGGACGATGCGG |
| 39 | ILL-PF3 A | ACACTCTTTCCCTACACGACGCTCTTCCGATCTTCGACGAGGACGATGCGG |
| 40 | ILL-PF4 A | ACACTCTTTCCCTACACGACGCTCTTCCGATCTGATCAGAGGACGATGCGG |
| 41 | ILL-PFU B | AATGATACGGCGACCACCGAGATCTACACTCTTTCCCTACACGACGCTCTTCCGATCT |
| 42 | ILL-PRU A | ATCTCGTATGCCGTCTTCTGCTTGTCTCGGATCCTCAGCGAGTC |
| 43 | ILL-PR2 B | GATCGGAAGAGCACACGTCTGAACTCCAGTCACCGATGTATCTCGTATGCCGTCTTCTGCTTG |
| 44 | ILL-PR1 B | GATCGGAAGAGCACACGTCTGAACTCCAGTCACATCACGATCTCGTATGCCGTCTTCTGCTTG |
| 45 | ILL-PR3 B | GATCGGAAGAGCACACGTCTGAACTCCAGTCACTGACCAATCTCGTATGCCGTCTTCTGCT |
| 46 | ILL-PR4 B | GATCGGAAGAGCACACGTCTGAACTCCAGTCACGCCAATATCTCGTATGCCGTCTTCTGCTTG |

FIG. 12

| Mouse Antibody | Clone | Company |
| --- | --- | --- |
| CD11b- PECY7 | M1/70 | BD |
| F4/80 FITC | A3-1 | AbD Serotec |
| LC6C PAC BLUE | AL-21 | BD |
| LY6G APC CY7 | 1-A8 | BD |
| IL4R -PE | mIL4R-M1 | BD |
| Live/Dead fixable dead cell stain | | Invitrogen |
| CD3 PERCP CY5.5 | 17A2 | eBioscience |
| CD4 PE | GK1.5 | BD |
| CD8 – PACIFIC BLUE | 53-6.7 | BD |
| CD3E percp | 145-2c11 | BD |
| CD11C PE CY7 | HL3 | BD |
| CD49B APC | DX5 | eBioscience |
| CD19 APC-CY7 | ID3 | BD |
| CD11B APC | M1/70 | BD |
| GRL PERCP 5.5 | RB6-8C5 | BD |
| F4/80 PE CY7 | BM8 | BD |
| DAPI | | Sigma-Aldrich |
| CD25 PE | 3C7 | BD |
| FOXP3 APC | FJK-16S | eBioscience |
| CD3 PERCP | 145-2C11 | BD |
| CD4 APC CY7 | GK1.5 | BD |
| CD8 pac blue | 53-6.7 | BD |
| Alexafluor 647 Streptavidin | | Biolegend |
| Alexafluor 750 Streptavidin | | Biolegend |
| Human antibodies | | |
| CD33-FITC | HIM3-4 | BD |
| IL4Ra-PE | 25463 | R&D |
| CD14-APCH7 | MφP9 | BD |
| CD15-BV711 | W6D3 | BD |
| HLADR-v500 | G46-6 | BD |
| CD11b-BV605 | ICRF44 | BD |

RNA APTAMERS AND USES THEREOF

CROSS-REFERENCE TO RELATED APPLICATIONS

This application claims the benefit of priority to U.S. Provisional Application No. 62/815,142, filed Mar. 7, 2019, the disclosure of which is incorporated herein by reference in its entirety.

STATEMENT ON U.S. GOVERNMENT INTEREST

This invention was made with government support under W81XWH-09-1-0048 awarded by The United States Department of Defense. The government has certain rights in the invention.

INCORPORATION BY REFERENCE OF MATERIALS SUBMITTED ELECTRONICALLY

This application contains, as a separate part of the disclosure, a Sequence Listing in computer readable form (Filename: 53952A_SubSeqListing.txt; Size: 13,594 bytes; Created: Jan. 8, 2026), which is incorporated by reference in its entirety.

BACKGROUND

Chemotherapy using different cytotoxic agents is the standard of care treatment for most human malignancies. However, these treatments are associated with moderate to serious toxicities that decrease the overall quality-of-life for patients with cancer and are often dose limiting and therefore responsible for modest therapeutic efficacy (1, 2). Drug delivery nanoplatforms aimed at concentrating the chemotherapeutic agent(s) at the tumor site(s) are gaining interest as modalities to decrease systemic toxicity and increase efficacy (2-4). However, most nanoplatforms rely either on physical properties of tumor vasculature, such as the enhanced permeability and retention (EPR) effect (5), or on the presence of markers characterizing the neoplastic cells. The EPR effect allows the preferential targeting of primary tumors and established metastases but is poorly effective against not-yet vascularized micro-metastases (6). Targeting an appropriate tumor-associated antigen allows drug delivery to disseminated neoplastic cells but may result in tumor editing (7, 8) rather than eradication, because of the genetic instability of neoplastic cells (9). An alternative and burgeoning strategy is the delivery of therapeutic agents to the genetically stable tumor stromal cells that characterize primary tumor, metastases, and pre-metastatic niches (10). Myeloid cells in the tumor microenvironment are an interesting target because they account for a large proportion of the tumor mass, they promote cancer cell survival and metastases (11-16), provide immune protection, and are recruited early during tumor progression in the primary tumor and in the pre-metastatic niches (17). Importantly, tumor-infiltrating myeloid cells (TIMC, comprising Myeloid Derived Suppressor Cells—MDSC, Tumor Associated Macrophages—TAM, neutrophils, and monocytes) express a peculiar activated, pro-tumoral phenotype that differentiates them from their systemic counterpart (18-22). Since markers expressed on TIMC but not on their circulating counterparts remain to be fully defined, we used an unsupervised approach to generate RNA aptamers against known and unknown TIMC-specific epitopes (23).

RNA aptamers penetrate deeply into the tissues, are non-immunogenic, and are easy to manufacture and engineer for improved pharmacokinetic and stability. Furthermore, these reagents can be selected to be rapidly internalized in the target cells (24), thus allowing specific drug (e.g., RNA therapeutics or small molecules) absorption in the desired cells. Finally, the combinatorial use of aptamers that each bind a different epitope in the target cell should increase the overall specificity and maximize drug delivery in the chosen tissue.

BRIEF DESCRIPTION OF THE FIGURES

FIG. 1A) FACS analysis of IL4-treated MSC2 stained with the Cy3-labelled RNA aptamers from cycle 0, as control, or cycle 11. FIG. 1B) FACS analysis of MSC2 or IL4 treated MSC2 with Cy3-labelled polyclonal aptamers from the indicated library. FIG. 1C) Single cell suspensions from the spleen or the tumor of mice bearing the CT26 colon carcinoma (0.5 cm in diameter) were stained with the polyclonal aptamer library and counterstained with antibodies against CD11b, Gr1, F4/80, CD11c, CD19, CD49b, CD4, and CD8. Data derived from one experiment representative of one another.

FIG. 2A) Single cell suspensions from spleens and tumors of mice pooled from 3 mice bearing the 4T1 tumor (0.5 cm in diameter) were labelled with antibodies against CD11b, Ly6C, Ly6G and the 15 Cy3-labelled monoclonal aptamers identified by APTANI. Data derived from n=5 biological replica and derived from n=2 independent experiments. Aptamers 3 (SEQ ID NO: 3), 6 (SEQ ID NO: 6), 11 (SEQ ID NO: 11), and 14 (SEQ ID NO: 14) were chosen for further analysis and are in bold. *=P<0.001 by one-way ANOVA and post-hoc Holm-Sidak comparisons versus irrelevant aptamer. Only background staining was observed in the CD11b− cells. FIG. 2B) Secondary structure of aptamers 3 (SEQ ID NO: 3), 6 (SEQ ID NO: 6), 11 (SEQ ID NO: 11), and 14 (SEQ ID NO: 14). Binding motifs identified by APTANI are underlined in black. Fluorinated nucleotides are highlighted in gray. FIG. 2C) An equimolar mixture of the aptamers increases the specificity for tumor infiltrating myeloid cells. Pooled single cell suspension of tumor or spleen from 4T1 bearing mice were labeled with aptamers 3 (SEQ ID NO: 3), 6 (SEQ ID NO: 6), 11 (SEQ ID NO: 11), and 14 (SEQ ID NO: 14), or equimolar mixtures of each aptamer and analyzed by FACS. Data derived from n=3 independent experiments.

FIG. 3A) Single cell suspension from the blood and the tumor of patients (n=3) with recurrent HNSCC was stained with AF647-labelled aptamers, anti-CD33, anti-CD14, anti-CD124 antibodies, and zombie vital dye and analyzed by flow cytometry. FIG. 3B) Image cytometry: Paraffin embedded tumor specimens from patients (n=5) with HNSCC undergoing salvage surgery were stained with an equimolar mixture of Cy3-labelled aptamer, FITC-anti-CD33 antibody, and DAPI and analyzed by cell profiler and FCS-express V6 after gating on the "tumor area" or "healthy tissue area" and either on CD33+ or CD33− cells. Aptamer MFI was normalized on the MFI of the all the cells in the corresponding region of interest. Approximately $10^6$ and $10^5$ cells were analyzed in the "tumor area" or "healthy tissue area" respectively. Significant paired T test are reported.

Figures 4A, 4B, 4C, 4D, 4E:
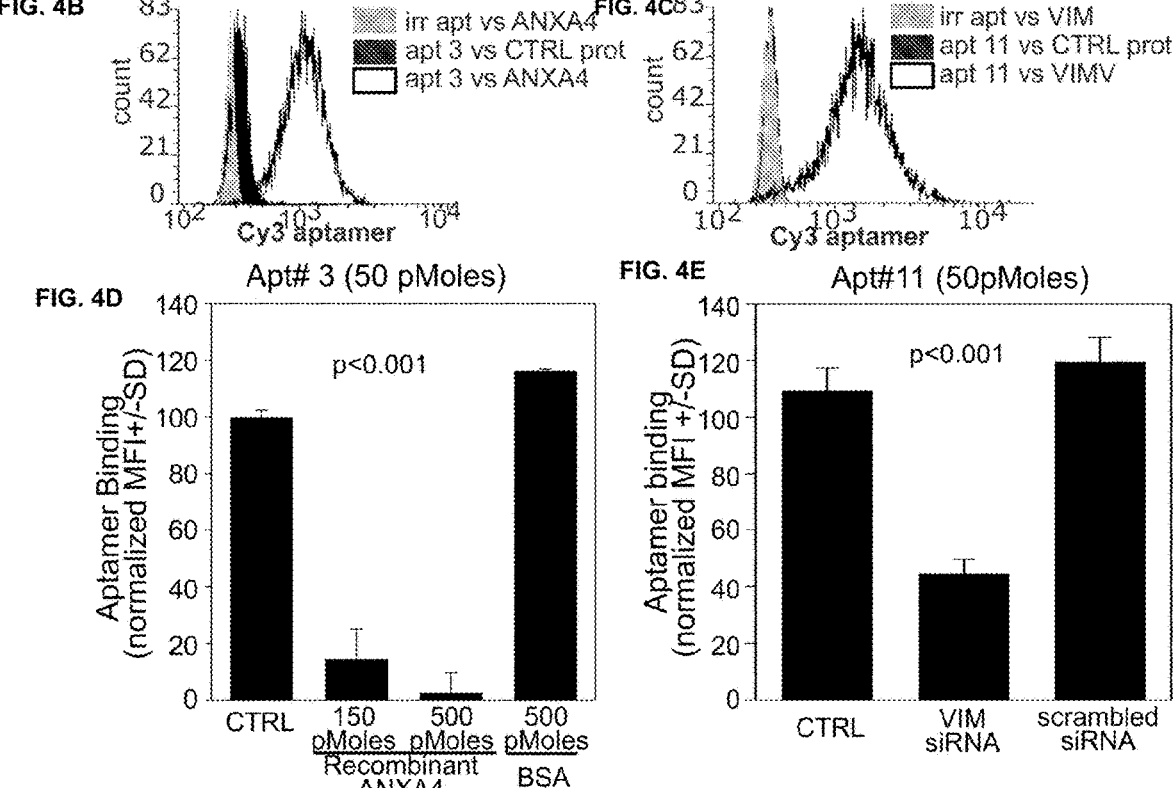

FIG. 4A-4E. Characteristics of aptamers that preferentially recognize tumor infiltrating myeloid cells. FIG. 4A) Affinity of the aptamers for IL4 treated MSC2 cells was determined by FACS. Putative targets (ANXA4 and VIM) were identified via aptamer-based immunoprecipitation, SDS page, and mass spec analysis. Kds against ligands was determined by FACS against recombinant protein conjugated to epoxy beads. FIG. 4B) Epoxy beads conjugated with ANXA4 or irrelevant protein were stained with Cy3-labelled aptamer 3 or irrelevant aptamer and analyzed by FACS. FIG. 4C) Epoxy beads conjugated with vimentin or irrelevant protein were stained with Cy3-labelled aptamer 11 or irrelevant aptamer and analyzed by FACS. FIG. 4D) ANXA4 competitive assay. $5 \times 10^5$ IL4 treated MSC2 were stained with aptamer 3 in the presence or in the absence of recombinant ANXA4. FIG. 4E) MCS2 cells were transfected via the 4PD nanoparticle with shRNA against vimentin or with a scrambled shRNA. 4 days later cells were stained with Cy3-labelled aptamer 11 and DAPI. Pa=One-way ANOVA p value. Data derived from n=2 independent experiments.

FIGS. 5A-5F. Aptamers target preferentially tumor stroma in vivo. FIG. 5A) Aptamers target tumors in vivo. Mice bearing the 4T1-luciferase mammary carcinoma were injected intravenously with an equimolar mixture of biotinylated aptamers 3, 6, 11, and 14 conjugated with AF750 streptavidin. FIG. 5B) Bio-distribution was evaluated by IVIS 2 h later. FIG. 5C) Time course analysis or aptamer bio-distribution performed by IVIS. FIG. 5D) Mice (n=5) bearing the 4T1 mammary carcinoma were injected i.v. with aptamers 3, 6, 11, and 14 loaded on AF-647 streptavidin. After two hours, the indicated organs were harvested, counterstained with antibodies against CD11b, CD19, CD49b, CD11c, and CD3.

FIG. 5E, FIG. 5F) Mice (n=5) were treated as in FIG. 5D, and aptamer distribution was evaluated by flow cytometry at different time points after counterstaining the single cell suspensions with antibodies against CD11b, F4/80, Ly6C, and Ly6G. *=one-way Anova p<0.001.

Figures 6A, 6B, 6C, 6D:
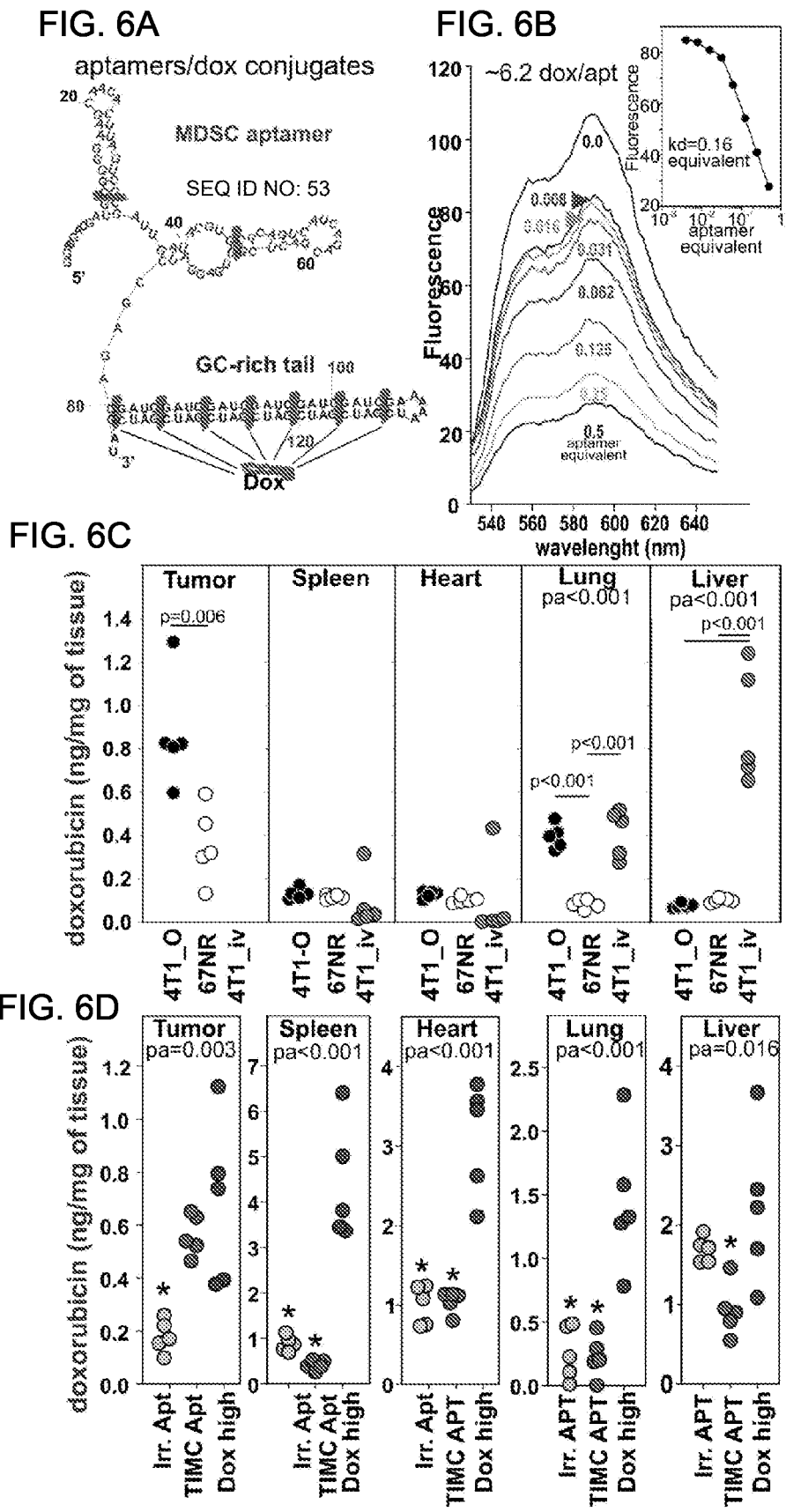

FIGS. 6A-6D. TIMC specific aptamers increase doxorubicin concentration at the tumor site. FIG. 6A) TIMC specific aptamers were conjugated to doxorubicin by extending the 3' end with a GC rich tail. FIG. 6B) Fluorescence spectra of doxorubicin solution (1.5 M) with increasing molar ratios of the TIMC aptamer equimolar mixture (from top to bottom: 0, 0.008, 0.016, 0.032, 0.062, 0.125, 0.25, and 0.5 equivalent). Inset: A Hill plot for the aptamer titration (Kd=0.16 equivalent; 6.2 dox molecules/aptamer). FIG. 6C) BALB/c mice (n=5) were challenged with the 4T1 mammary carcinoma orthotopically (4T1_o; primary tumor: breast, metastases: lung) or intravenously (4T1_iv; metastasis in the lung and in the liver). An additional group of mice was challenged orthotopically with the non-metastatic, 4T1 derived, cell line 67NR (only primary tumor). 10 days later, mice were treated intravenously with doxorubicin (0.35 mg/kg) conjugated with TIMC specific aptamer. Doxorubicin bio-distribution was evaluated 24 h later. Data derived from one experiment representative of another one. FIG. 6D) Bio-distribution of free doxorubicin or doxorubicin given via TIMC specific or control aptamer. Mice (n=5) bearing the 4T1 mammary carcinoma (0.5 cm in diameter) in the third mammary gland were given i.v. free doxorubicin (Dox high 3.5 mg/kg), TIMC-aptamer conjugated doxorubicin (TIMC apt; 0.35 mg/kg) or irrelevant aptamer (Irr. Apt) conjugated doxorubicin. 24 h later doxorubicin in the tissues was quantified by spectrometry after acid alcohol extraction. Data derived from 1 experiments representative of another one. *=p<0.05 in multiple pairwise comparison vs dox high group (Holm-Sidak method).

Figures 7A, 7B, 7C:
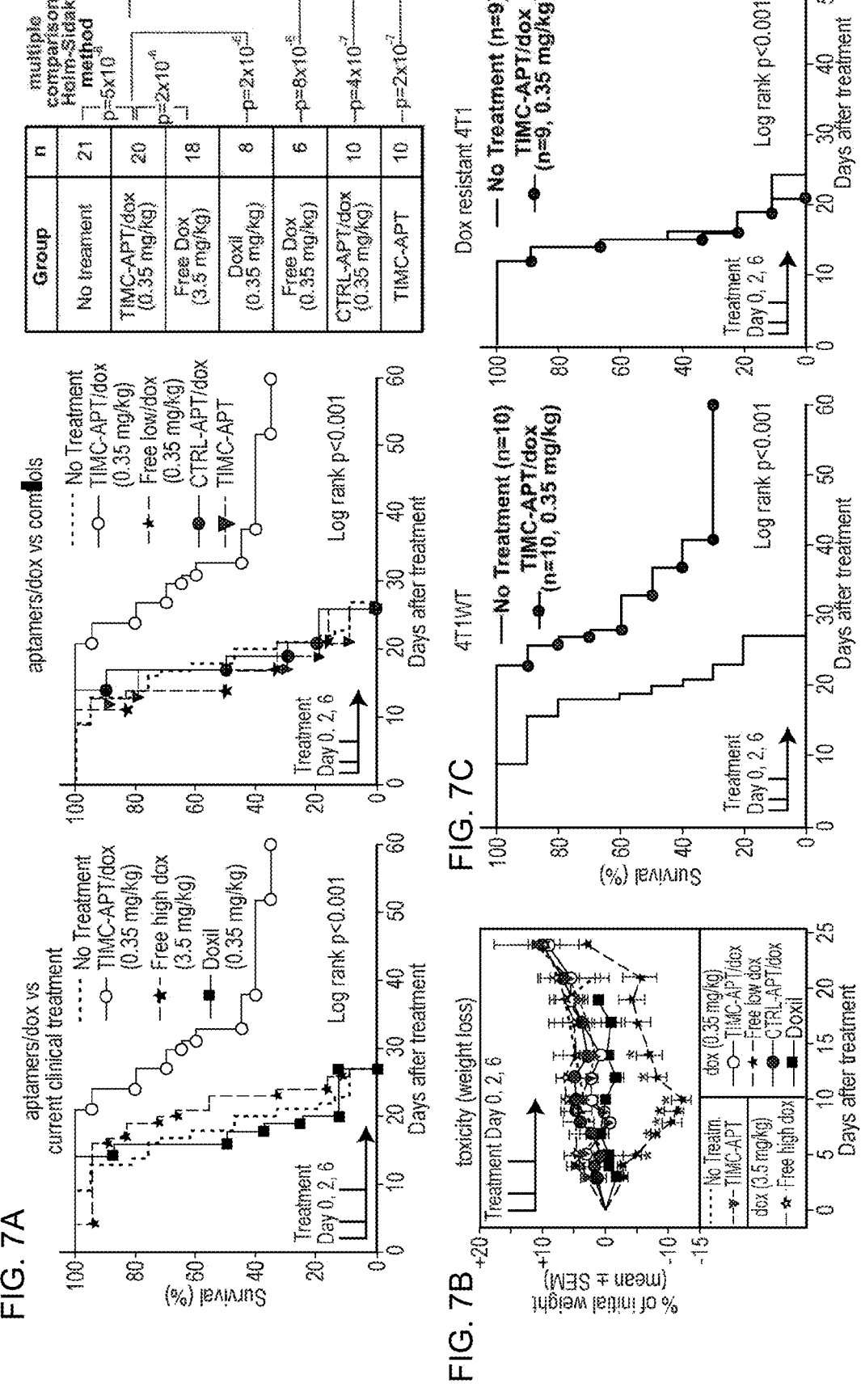

FIGS. 7A-7C. TIMC-specific aptamers increase doxorubicin therapeutic index. A) Mice bearing the 4T1 tumor in the third mammary gland were treated i.v. with free doxorubicin (3.5 mg/kg or 0.35 mg/kg), with Doxil (0.35 mg/kg), or doxorubicin conjugated to TIMC-specific aptamer mix (0.35 mg/kg). Additional controls included irrelevant aptamers conjugated with doxorubicin, unconjugated TIMC specific aptamers, and untreated mice. Treatment was repeated 2 and 6 days later. Mice were euthanized when tumor index reached 1.2 cm$^2$. Log-rank and post-hoc multiple comparison analysis (Holm-Sidak method) is reported. Weight loss as measure of toxicity is reported. C) BALB/c mice were challenged with the 4T1wt breast cancer or with the doxorubicin resistant variant dox-resistant 4T1. When tumor reached 0.5 cm in diameter, mice treated with TIMC specific aptamers or left untreated. Survival was monitored.

Figure 8A:
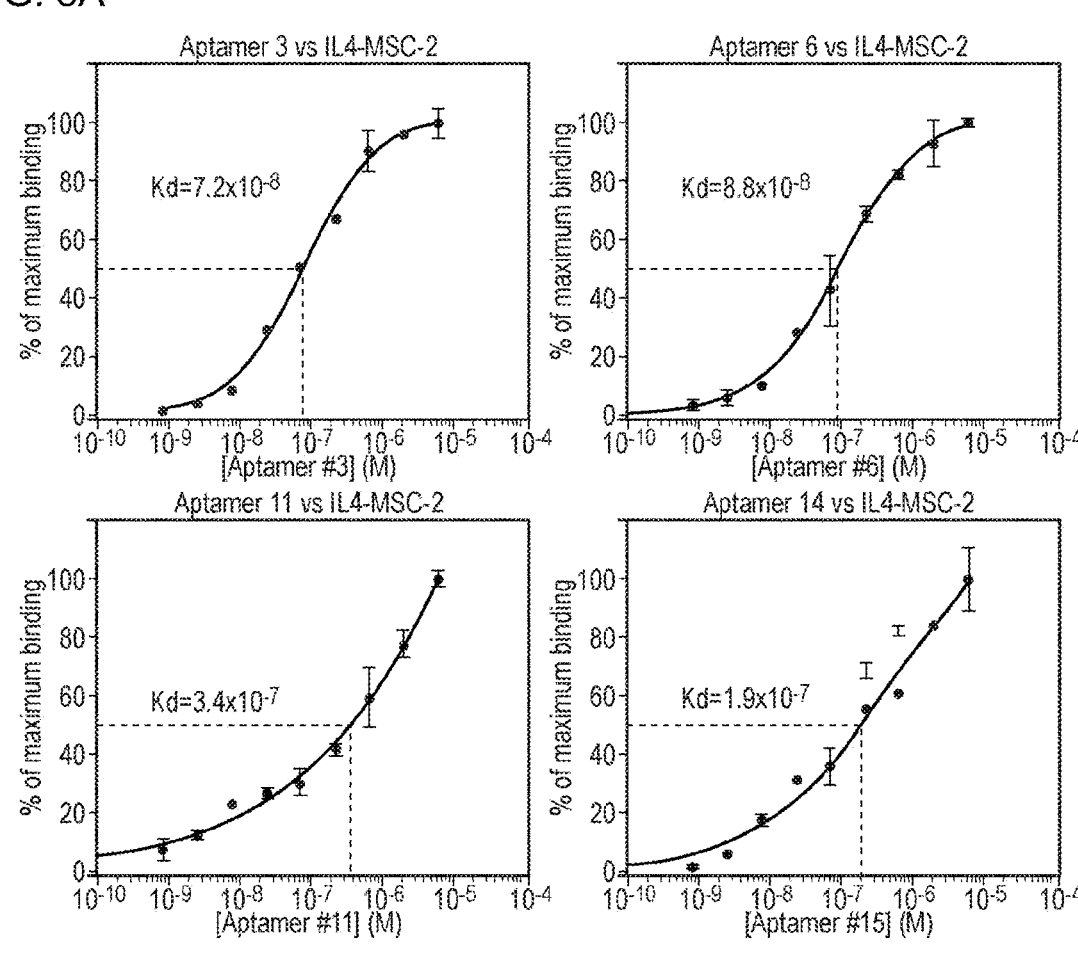
Figure 8B:
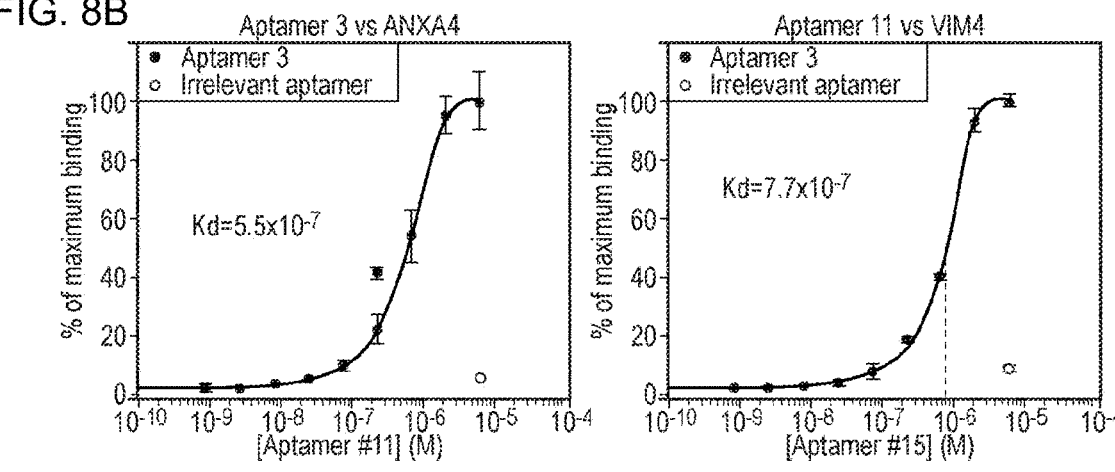

FIG. 8A and FIG. 8B. Affinity of aptamers #3 (SEQ ID NO: 3), #6 (SEQ ID NO: 6), #11 (SEQ ID NO: 11) and #14 (SEQ ID NO: 14) for IL4 treated MSC2 or their putative ligand. FIG. 9A) $10^5$ IL4-treated MSC2 were stained with different concentration of the indicated, Cy3 labelled aptamers. Binding was evaluated by FACS. FIG. 9B) Different concentration of Cy3 labelled aptamer #3 and aptamer #4 were used to stain epoxybeads conjugated with recombinant ANXA4 or recombinant VIM, respectively. The Cy3 labelled aptamer against IL4Ra was used as a irrelevant control. Binding was evaluated by FACS. Data derived from three independent experiments.

Figure 9:
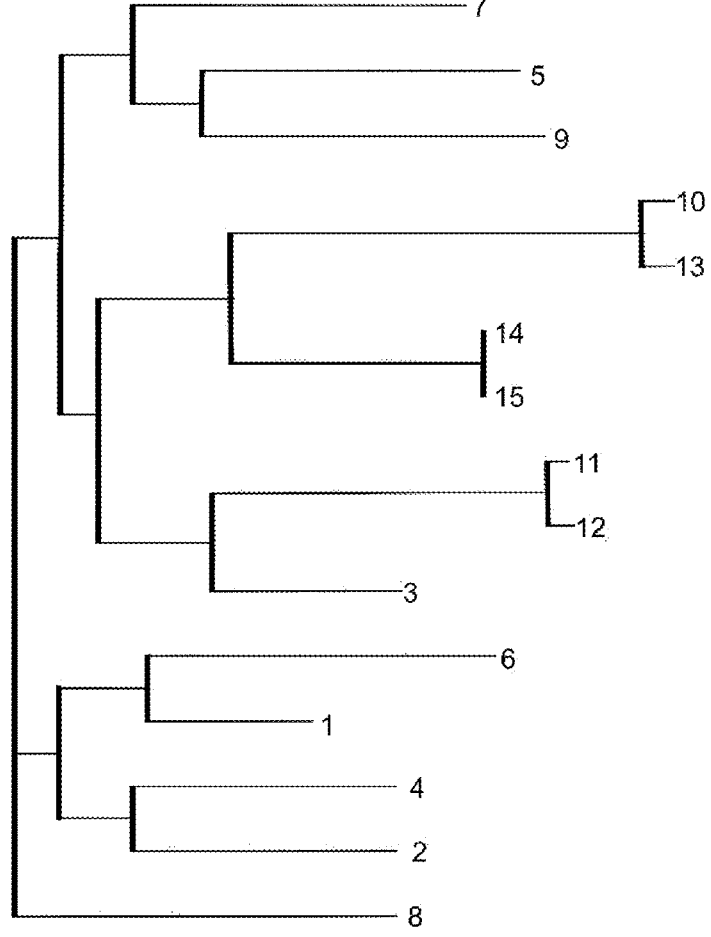

FIG. 9. Cluster analysis of the 15 aptamers chosen with APTANI. The variable regions of the 15 monoclonal aptamers chosen with APTANI were aligned with clustal-Q and neighbor-joining tree generated with Jailview using default parameters.

FIG. 10. Sequence, frequency, and motifs of 15 aptamers selected by APTANI based on an enrichment of at least 0.1% and the presence of at least three motifs or of at least one motif with a frequency higher than 0.1%.

FIG. 11 Oligonucleotides used in the Examples.

FIG. 12. List of mouse and human antibodies used in the Examples.

DETAILED DESCRIPTION

There present disclosure is based, in part, on the discovery of RNA aptamers that specifically recognize tumor infiltrating myeloid cells (TIMC) across different preclinical models and, more importantly, in humans.

Systemic chemotherapy remains one of the most important treatments for cancer therapy, but it comes with systemic side effects, such as cardiotoxicity and profound neutropenia that impose limits on the use of this therapeutic option (38). Additionally, chemotherapy induces long-term morbidity that decreases the quality of life of cancer survivors.

Described herein is a new mode by which chemotherapeutic or other therapeutic agents (e.g., RNA therapeutics) can be concentrated in the tumor and in the metastatic sites by physically targeting the pro-tumoral activated phenotype of tumor-infiltrating myeloid cells. Myeloid cells are the most abundant innate immune cells present in the stroma of several types of mouse and human cancer (39-41). The presence of myeloid cells in human tumors correlates with increased vascular density, higher metastatic spread, and a worse clinical outcome, and their presence is necessary for tumor progression (42, 43). At the tumor site, myeloid cells acquire unique antigenic profiles and functional characteristics that differentiate them from their systemically circulating cell counterparts, and are necessary for their immune suppressive, tolerogenic, and pro-tumoral roles (20, 44, 45). Although, many approaches have been and are being tested to inhibit the mechanisms that myeloid cells employ to promote tumor progression or their interaction with the neoplastic cells (46-48), to our knowledge no reagent able to discriminate between tumor infiltrating and circulating myeloid cells is yet available. Furthermore, although aptamers and peptides able to bind both tumor-associated and circulating MDSC in mice has been isolated (49-51) and employed for MDSC depletion (50, 51) or to improve Doxil delivery (49), these reagents did not recognize preferentially tumor infiltrating myeloid cells. Indeed, when used for Doxil delivery an important accumulation of Dox in the heart and in the spleen and liver was noted (49).

Four RNA aptamers (aptamer 3, 6, 11, and 14, FIG. 2) were isolated that were specific for the tumor-infiltrating myeloid cells but not for their circulating counterparts regardless of the used tumor model or mouse strain. Interestingly, aptamer 3 and aptamer 11 have ANXA4 and Vimentin as their ligands, respectively. Vimentin plays a key role in monocyte differentiation and in the production of reactive oxygen species and, under pro-inflammatory stimuli, translocates to the membrane of activated macrophages (52-56). Indeed, vimentin is present in the tumor stroma of different cancers, but it is poorly expressed in cultured tumor cells (54-56). Functionally, this protein has been involved in epithelial-mesenchymal transition and metastasis (57). ANXA4 is a calcium-dependent, phospholipid-binding protein that promotes membrane fusion and exocytosis (58). It is overexpressed in activated MDSCs, in TIMC, and activated M2 macrophages (44, 59). Although localized in the cytoplasm in resting macrophages, ANXA4 translocates to the membrane during activation (60, 61). Both proteins are expressed in human malignancies and their expression correlates with a worse prognosis in renal, breast and ovarian cancer according to the TCGA data and the Protein Atlas. Thus, both identified targets support the specificity of the aptamers for TIMC activated phenotypes.

Aptamers described herein cross-react with and recognize preferentially human MDSC in the tumor but not in the blood of patients with HNSCC suggesting their possible use for MDSCs detection or as tumor targeting agents in human malignancies. Indeed, the combinatorial use of these four aptamers offers an efficient delivery of the chemotherapeutic agent, e.g., doxorubicin, or RNA therapeutic agent (e.g., siRNA against CCR1 and CCR5, in our proof-of-principle experiments, to the primary and metastatic tumor site with virtually no drug accumulation in other tissues. In a therapeutic setting our approach is far superior to free doxorubicin or Doxil (34, 35) (today's gold standard for doxorubicin targeted delivery) and results in tumor regression in approximately 40% of treated mice with no observed systemic toxicity.

Taken together, the data provided herein indicates that it is possible to potentiate the therapeutic index of chemotherapeutic agents by targeting the surface protein profile of tumor-infiltrating myeloid cells, allowing the bystander release of the drug within the tumor microenvironment. While combinatorial use of aptamers described herein is not required (i.e., the use of a single aptamer is contemplated), the combinatorial use of several different aptamers as a means of chemotherapeutic agent delivery, each targeting different TIMC specific epitopes, significantly increases treatment specificity, improve efficacy, and reduce the toxicity of chemotherapeutic agents as compared with the systemic delivery of these agents in current, clinically available treatment modalities.

The disclosure provides an RNA aptamer is conjugated to a therapeutic, wherein the aptamer specifically binds to a target expressed on a tumor-infiltrating myeloid cell. In various aspects, the therapeutic is a nucleic acid molecule (e.g., DNA, RNA, shRNA, siRNA or miRNA). In various aspects, the therapeutic is a chemotherapeutic agent (e.g., doxorubicin). The target expressed on the tumor-infiltrating myeloid cell is optionally annexin or vimentin. The disclosure further provides a method of delivering a therapeutic to a tumor-infiltrating myeloid cell comprising contacting the cell with the aptamer. The disclosure also provides a method for detecting the presence of a tumor-infiltrating myeloid cell in a biological sample, comprising contacting the sample with the aptamer conjugated to a detectable label. The disclosure additionally provides a method of treating cancer in a subject in need thereof, comprising administering the aptamer to the subject. The subject is optionally suffering from breast cancer, colon cancer, or renal cancer.

EXAMPLES

Materials and Methods

Study Design and rigor: The goal of this study was to identify RNA aptamers able to discriminate myeloid cells infiltrating the tumor from those in the periphery. Aptamers were selected by unsupervised Cell-SELEX, bioinformatics analysis, and empirical testing by flow cytometry and immune fluorescence analysis. Each experiment has been performed at least twice by two independent experimentalists and, if possible, the same phenomenon was evaluated using two independent techniques to eliminate assay specific artifacts. Flow cytometry was performed on a daily-calibrated flow cytometer, using titrated and validated antibody control, vital dye, automatic compensation using single cell color, and FMO or control aptamer (cycle 0 or irrelevant aptamer) as negative controls. For in vivo experiments, mice were randomized before treatment and tumor measurement was taken by an experimentalist blind to the treatment. Unless otherwise specified, mice were euthanized when tumor reached ~1.2 cm of diameter, or if they lost more than 20% of initial body weight or showed clinical signs of treatment related toxicity (i.e., lethargic mice, ruffled coat etc.). Data are cumulative and derived from 2 to 3 replicate experiments each with 3-5 mice per group. Group size was determined by power analysis using the effect size from pilot experiments. Outliers are always included in the data. In one experiment, two mice were removed and euthanized for study unrelated reasons (i.e., wounds from fights).

Cell lines and recombinant proteins: 4T1(62), 4T1HAThy1.1luciferase(63), TS/A(64), MSC2(26), CT26 (65), Renca(66), MCA203(67), and 67NR(68) cell lines were previously described. All cell lines were maintained in complete media (RPMI (Gibco), supplemented with HEPES (10 mM), streptomycin (150 U/mL), penicillin (200 U/mL), 10% heat-inactivated FBS (Invitrogen), and Beta-mercaptol (20 μM)).

DOXR-4T1 was selected from the parental cell line by culturing the cells with increased dosage of DOX. The resulting DOXR-4T1 cell line was maintained in complete media supplemented with doxorubicin (3.5 μg/ml).

MSC2 were treated with IL4 as previously described (26) by incubating $5\times10^5$ cells in a T75 flask (Falcon) for 4 days with rmIL4 (100 ng/ml, Peprotech) in 20 ml of complete media. Annexin A4 and vimentin recombinant proteins were purchased from myBiosource.

Microarray gene expression profiling of MSC2 and CD11b[+] cells: After four days of culture with or without IL4, MSC2 were washed with PBS prior to RNA extraction. For each chip, 2.5 μg of total RNA, Trizol extracted and cleaned with RNeasy Qiagen columns, were amplified to biotinylated complementary RNA (cRNA) as described in the Affymetrix GeneChip® Expression Analysis Technical Manual. All the pre-hybridization quality controls were performed with the Agilent 2100 bioanalyzer (Agilent Technologies). RNA from 5 biological replicates of MSC2 and MSC2 cells treated with IL4 was then hybridized on Affymetrix mouse genome expression MG-U74Av2 arrays. Microarray probe fluorescence signals were converted to $\log_2$ expression values using the Robust Multiarray Average procedure of the affy Bioconductor package. Fluorescence intensities were background-adjusted and normalized using quantile normalization, and expression values were calculated using median polish summarization and the custom chip definition file for the mouse array MG-U74Av2 based on Entrez genes (mgu74av2_Mm_ENTREZG version 21.0.0; brainarray.mbni.med.umich.edu/Brainarray/Database/CustomCDF/21.0.0/entrezg.asp) for a total of 8,124 custom probe sets. Microarray data are available form Gene Expression Omnibus GSE110774.

CD11b[+] cells were magnetically isolated from single suspension of the spleen or the tumor mice challenged 9 days before with C26GM. Purity was higher than 95% as per flow cytometry analysis. For each chip, 2.5 μg of total RNA, Trizol extracted and cleaned with RNeasy Qiagen columns, were amplified to biotinylated cRNA as described in the Affymetrix GeneChip® Expression Analysis Technical Manual. All the pre-hybridization quality controls were performed with the Agilent 2100 bioanalyzer (Agilent Technologies). RNA from 6 biological replicates of CD11b[+] cells from the tumor and from the spleen was then hybridized on Affymetrix mouse genome expression MOE4302 arrays. Microarray probe fluorescence signals were converted to log 2 expression values using the Robust Multiarray Average procedure of the affy Bioconductor package. Fluorescence intensities were background-adjusted and normalized using quantile normalization, and expression values were calculated using median polish summarization and the custom chip definition file for the mouse array MOE4302 based on Entrez genes (mouse4302_Mm_ENTREZG version 21.0.0; brainarray.mbni.med.umich.edu/Brainarray/Database/CustomCDF/21.0.0/entrezg.asp) for a total of 18,139 custom probe sets. Microarray data are available form Gene Expression Omnibus GSE110774. MSC2 and CD11b dataset were then merged using 7,860 common Entrez gene identifiers and the merged dataset batch-corrected using the ComBat function of Bioconductor sva package. To identify genes overexpressed in MSC2 treated with IL4 and CD11b[+] cells from the tumor, we compared the expression levels of IL4-treated MSC2 with those of untreated cells (and of CD11b[+] cells from tumor with those of cells from spleen) using Significance Analysis of Microarray (SAM) algorithm coded in the samr R package. In SAM, we estimated the percentage of false-positive predictions (i.e., false discovery rate, FDR) with 100 permutations and selected as differentially expressed those probe sets with an FDR q-value ≤0.05 and an absolute fold change ≥2. Global unsupervised clustering was performed using the function hclust of R stats package with Pearson correlation as distance metric and average agglomeration method. Statistical significance of the clustering has been computed in terms of approximately unbiased p-value using the cluster.bootstrap function of the R pvclust package. Gene expression heatmaps have been generated using the function heatmap.2 of R gplots package after row-wise standardization of the expression values. All data analyses were performed in R version 3.3.3 using Bioconductor libraries and R statistical packages.

Aptamer selection: The cDNA random library (previously described by the Sullenger group (69), was synthetized by Eurofins technology and amplified by PCR using recombinant Taq (Invitrogen)) with the SRlong and the SF primers (FIG. 11) with the following cycling condition: 95° C. 5', 3× (94° C. 30", 52° C. 20", 72° C. 25"), 20× (94° C. 30", 54° C. 20", 72° C. 25"), 72° C. 5'. Amplified DNA was purified using the PCR purification kit (Qiagen) and transcribed in vitro by Durascribe T7 RNA synthesis kit (Epicentre, Madison, WI, USA) or APT-GET T7 transcription kit. The resulting 2'Fluoro-RNA aptamers were purified using the RNeasy kit (Qiagen). In the initial round of selection, 27 pmoles of RNA were resuspended in 450 μl PBS (pH 7.4, Life technologies, MO, USA), heated at 65° C. for 5' and then cooled at room temperature (RT) for at least 10'. The RNA aptamer library was first incubated at RT in PBS (1 ml) for 10' on a rotator with $2\times10^6$ MSC2 cells as negative selector. ryCells were then spun down (514 g, 10'), and supernatant filtered (0.2 μm supor membrane, Pall Corporation) to remove residual cells and to recover unbound aptamers. Unbound aptamers were incubated with IL4 treated MSC2 ($0.5\times10^6$) as positive selector in PBS with yeast RNA (10 ug/ml, Ambion) for 10' at RT on a rotator. Cells were spun down (514 g, 10') and washed 3 times (3' wash) with 1 ml of PBS with $MgCl_2$ (0.5 mM $MgCl_2$, 1 mM $CaCl_2$)). Total RNA was then isolated with Trizol (Invitrogen) and reverse transcribed in cDNA with SuperScript® III Reverse Transcriptase kit following manufacturer's instructions (Invitrogen) and SR oligonucleotide. The resulting cDNA was amplified by PCR (95° C., 5', 3× (94° C. 30", 52° C. 20", 72° C. 25"), 15× (94° C. 30", 54° C. 20", 72° C. 25"), 72° C. 5) using the SF and SRshort primers (FIG. 11). Amplified DNA was purified with the PCR purification kit (Qiagen), transcribed using the DurascribeT7 kit and the resulting RNA aptamers were purified with RNeasy mini kit (Qiagen) and used for the next cycle of selection. To increase stringency, starting at the sixth round of selection, incubation time with the IL4-treated MSC2 was reduced to 5', 5 washes were performed. Additionally, a reduced number of cells ($3\times10^5$ in cycle 6 and 7, $2.5\times10^5$ in cycle 8-10, and $2\times10^5$ in cycle 11) was used as positive selector to promote competition between aptamers with the same specificity and possibly isolate the most affine. Monoclonal aptamers were either synthetized by PCR and T7RNA polymerase using the DNA primers described in FIG. 12 or synthetized with a biotin on the 5' end by Boston Open Labs.

Flow cytometry: Aptamers were labeled with Cy3 using the Silencer siRNA Labeling Kit—Cy3 (Ambion) and 37 pmoles were used to label $5\times10^6$ cells unless otherwise specified. In some experiments biotinylated aptamers were labelled with streptavidin conjugated with Alexa Fluor 647 or Alexa Fluor 750 and purified from unbound aptamer by Ultra-4 centrifugal filters, 50,000 kDa (Millipore).

Antibodies used are summarized in FIG. 12. Dead cells were excluded by the analysis by using 4',6'-diamidino-2-phenylindole (DAPI; Sigma) or Live/Dead dye (Invitrogen).

Samples were read on a LSR2 equipped with 405 nm, 488 nm, 532 nm, and 635 nm lasers (BD Bioscience). Data were analyzed using FCS6 express software (Denovo-Software).

Immunofluorescence microscopy and Image cytometry: Fresh frozen tissue and tissues microarrays (AMSBIO) were fixed in 10% neutral-buffered formalin (BDH) for 15' at RT, incubated with dextran sulfate sodium/PBS (1:2 m/V— Pharmacia biotech) for 30' and washed with PBS. Tissues were then stained with Cy3-labelled aptamer (10 ug/ml) in PBS for 30', masked with 2% BSA, and counterstained with antibodies and/or DAPI.

Formalin-fixed tissues were deparaffinized with xylene (2×10' incubations) and rehydrated first with xylene/ethanol (1:1 v:v, 10' at RT) and then subsequentially incubated for 10' with the following ETOH solution: 100%, 100%, 95%, 90%, and 75%. Antigen retrieval was performed with Citrate buffer (pH6 Thermo-Fisher) by microwaving the tissue for 30 minutes at 100 W. Tissues incubated in PBS O/N at RT, incubated with dextran sulfate sodium/PBS (1:2 m/V— Pharmacia biotech) for 30' washed with PBS, and then stained with Cy3-labelled aptamer (10 ug/ml) in PBS for 30', masked with 2% BSA, and counterstained with antibodies and/or DAPI.

Whole stained tissue sections were scanned at 20× with the Olympus VS120 equipped with DAPI CUBE 455 nm (12.941 ms), a FITC CUBE 518 nm (410.271 ms) and a TRITC CUBE 580 nm (592.6 ms). Images were exported with OlyVIA software as single channel with a resolution of 5×, evaluated with ImageJ (fiji.sc/), tiled at 600×600 pixels with ImageSlicer (www.coolutils.com/) and processed with cell-profiler (www.cellprofiler.com) as follow: Nuclei were identified using the blue (DAPI) channel as primary object using the three classes Otsu Adaptive threshold method (correction factor of 1 threshold 0.1-1.0) with diameter between 2 and 10 pixels. Object declumping was based on shape and the size with default smoothing and distance parameters. Cells as secondary objects were segmented using fluorescence from the 3 merged channels by the three classes Otzu Adaptive threshold propagation method (threshold correction factor 0.0-1.0; regularization factor=0.02). Cytoplasm as tertiary object was identified as the area included in the cells (secondary object) but not in the nuclei (primary object). The resulting cpout files were analyzed with FCS Express 6 plus (www.denovosoftware-.com) by evaluating aptamers' fluorescence intensity in the CD33+ or CD33− cells in the tumor and in the surrounding healthy tissue identified on serial H&E section by an experience pathologist.

HNSCC specimens: Specimens and blood from patients (median age 59 years, range 49-72) with recurrent stage 3 or 4 HNSCC of the oral or oropharynx cavity undergoing salvage surgery were collected at the time of surgery or biopsy under a clinical protocol approved by the University of Miami.

shRNA transfection: 2×10⁵ MSC2 were transfected with 1 μg of vimentin specific shRNA(29) (GCG CAA GAU AGA UUU GGA AUA UUC AAG AGA UAU UCC AAA UCU AUC UUG CGC UU—SEQ ID NO: 47) or scrambled shRNA using the 4PD MDSCs transfection kit (Kerafast) and following manufacturer instruction(30). Transfected cells were treated for 30' with mytomicin C (10 μg/ml) washed twice and incubated in a 6 well plate for 4 days (37° C., 5% CO2) with IL4 (100 ng/ml, Peprotech).

Preparation of polyclonal library for HT-sequencing: cDNA of cycles 1, 6, 10, and 11 were tagged using two sequential PCRs. The first PCR reactions were performed in 100 μl of water containing 1×PCR buffer, MgCl₂ solution (1.5 mM), dNTPs (200 μM each), DNA template (5 ng/μl) recombinant Taq polymerase (5 U, Invitrogen) and the PFA and PRA primers corresponding to each cycle described above. The reactions were performed in the GS482 thermo-cycler (G-STORM) using the following program: 95° C. 5', 5× (95° C. 1', 56° C. 30″, 72° C. 30″), 72° C. 10'. PCR was purified via gel extraction using the QIAquick Gel Extraction Kit (QIAGEN) following manufacturer instructions. The second PCR was performed using the same condition described above but using the UFB and PRB primers (Supplementary Table 2) and the following program: 95° C. 5', 6×(95° C. 30″, 65° C. 30″, 72° C. 30″), 72° C. 10'. Products were purified by gel extraction, quality and quantity evaluated via bio-analyzer (Agilent). Library quantitation and pooling took place at the Hussman Institute for Human Genomics-Center for Genome Technology using the KAPA Library Quantification Kit for Illumina platforms (part #KK4854). 10-13 μM of pooled samples were loaded on the Illumina cBot for cluster generation according to manufacturer's recommendations. Sequencing was performed on an Illumina HiSeq 2000/2500 (HCS 2.0.12.0) using the reagents provided in the Illumina TruSeq PE Cluster Kit v3 and the TruSeq SBS Kit-HS (200 cycle) kit. Data processing was done using HiSeq's Real Time Analysis (RTA) from Casava software. Base calling files were transformed into zipped FASTQ files containing raw reads with base qualities. These raw read files were then filtered by Illumina's internal filter resulting in 2 FASTQ files (1 per read) containing all pass-filter reads. FASTQ files were used as input to APTANI(27).

Bioinformatics selection of aptamers using APTANI: Aptamers were selected using APTANI, a computational method for the identification of target-specific aptamers from HT-SELEX data and secondary structure information (27). Briefly, APTANI first calculates the relative enrichment of each individual aptamer sequence produced by the HT-SELEX process and then, for each aptamer with an enrichment higher than a pre-selected threshold, predicts all secondary structures in a specific energy range and extracts the motifs represented in these structures. As a result, APTANI returns a list of aptamers, ranked by their abundance and by the presence of structural motifs. Here APTANI was used with default parameters on HT-SELEX data from cycles 1, 6, 10, and 11 and set the enrichment and motif frequency thresholds to 0.01% and 0.05%, respectively. Since at each run APTANI randomly samples 20% of the library to reduce the computational load, each analysis was replicated n=5 times and pooled the results to fully cover the entire library.

Mice: All animal experiments were approved by the Division of Veterinary Resources and the Institutional Animal Care & Use Committee of the University of Miami. 8-10 weeks old BALB/c and C57Bl/6J mice were purchased from Jackson Laboratories and maintain in the pathogen free animal facilities at the University of Miami on a chlorophyll free diet. Mice were allowed to acclimate for at least one week before experiments, ear-tagged, and randomized after tumor inoculation.

Aptamer-Doxorubicin treatment: Aptamer-doxorubicin was prepared by making DNA template with the appropriate aptamer followed by a GC-rich primer sequence downstream (GC rich Sul3', FIG. 11. From this template, RNA was transcribed and purified as described above. Doxorubicin (Sigma) was mixed with the RNA sequence as needed. Doxil (ALZA corporation) was purchased through the University of Miami pharmacy.

BALB/c mice were injected IV with the 4T1 luciferase thy1.1 tumor cell line. Treatment was started when tumors reached 5 mm of diameter and repeated 2 and 6 days later. Tumor growth and mice weight was reported. Mice were evaluated at least 3 times a week and humanely euthanized when tumor size index reached 150 $mm^2$ or if they lose >20% of initial weight due to chemotherapy or tumor growth in compliance with the IACUC policy and animal protocol. Data are expressed as tumor size index defined as the product of the main diameter with the perpendicular one.

IVIS analysis: Isofluorane-anesthetized, tumor-bearing mice were analyzed by the In Vivo Imaging System (Xenogen IVIS Spectrum—Perkin Elmer) 2 h after i.v. injection of 5' biotinylated aptamers conjugated with Alexa Fluor-750 (AF750) streptavidin (13.6 pmol/g) with an imaging stage heated at 37° C. 15' before imaging mice were injected intraperitoneal with D-luciferine (150 µg/g). AF750 fluorescence was read at 800 nm after excitation at 748 nm. Raw signal was subject to spectral unmixing to remove background fluorescence signal and AF750 fluorescence was quantified with the living Image v4.3 software (Perkin Elmer).

Detection of doxorubicin in tissue: The fluorescent properties of doxorubicin were used to quantify doxorubicin in tumor, liver, spleen, and lung as previously described(70). Briefly, tissues were harvested, weighed, and homogenized in acid alcohol (0.3N HCl solution, 70% EtOH), and doxorubicin was extracted over night at 4° C. Homogenate was spun down and supernatant samples were quantified by fluorometry (SpectraMax M5, Molecular Devices) using an excitation wavelength of 470 nm and measuring the intensity of emission at 590 nm and plotted on a standard curve of doxorubicin serially diluted in acid alcohol. Results were normalized on tissue weight.

Statistical analyses: All values depicted represent mean±standard deviation of biological replica unless otherwise indicated in the figure legend. Statistical calculations were performed by a person blinded to the treatment group using Sigmaplot 12.5 (Systat software). Statistical tests (one way ANOVA followed by Holm Sidak test for multiple pairwise comparison or student T test) were applied as indicated in the figure legends in a two-sided, unpaired fashion after normality was evaluated by the Shapiro-Wilk test. The variance was similar between experimental groups in each experiment unless otherwise stated. In vivo experiments included cohorts of the size indicated in each figure legend but at least 6 mice per group. In vitro analyses and in vivo experiments were repeated two to five times to ensure reproducible conclusions; the exact number of repetitions is stated in each figure legend. Log-rank test was used for survival analysis followed by all pairwise multiple comparison procedures (Holm-Sidak method). Data from multiple experiments were cumulated unless otherwise indicated in the figure legends. No experimental data point was excluded from analysis. Sample size was chosen by power analysis using effect size determined by pilot experiments or prior experience of the authors.

Example 1—Identification of Aptamers Specific for Tumor-Infiltrating Myeloid Cells To identify TIMC-specific aptamers, an unsupervised, high-throughput (HT) sequencing-cell SELEX (systematic evolution of ligands by exponential enrichment) (25) was performed using the MDSC-derived cell line MSC2 (26), followed by an empirical selection of monoclonal aptamer binding TIMC but not the splenic counterpart.

MSC2 cells were considered a suitable TIMC surrogate for the initial aptamer's screening since these cells are available without requiring any artifact-causing manipulation of tumor-infiltrating cells, and they acquire the suppressive activity only after treatment with IL4 (26). Furthermore, as confirmed by a genome-wide transcriptional analysis, MSC2 cells express genes that are shared with TIMC. Indeed, MSC2 cells treated with IL4 are transcriptionally similar to TIMC, both in terms of genome-wide expression levels and overexpressed genes, while untreated MSC2 share the gene expression profiles of splenic CD11b$^+$ cells.

Figures 1A, 1B, 1C:
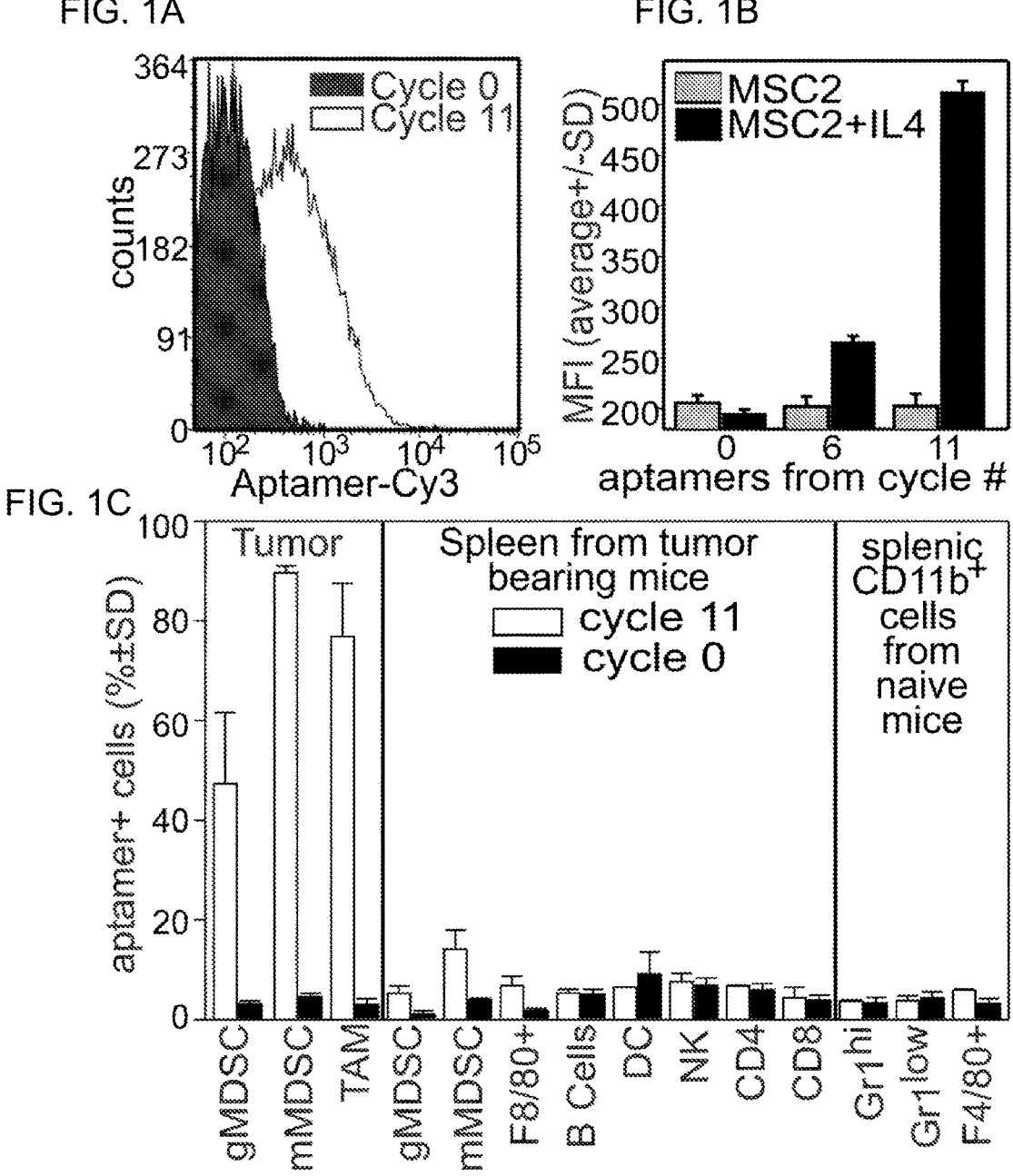
FIGS. 1A-1C. Selection of polyclonal aptamers specific for tumor infiltrating myeloid cells. HT-Cell SELEX was performed on MSC2 cells treated with IL4 or left untreated as a proxy of tumor infiltrating and splenic myeloid cells, respectively.

Aptamers were selected through 11 cycles of Cell-SELEX using untreated MSC2 as negative selector and IL4-treated MSC2 as positive selector, i.e. as TIMC surrogate. The resulting polyclonal aptamer library displayed a specificity increasing with the selection cycle (FIG. 1A) only for IL4-treated MSC2, thus proving the overall efficacy of the SELEX enrichment (FIGS. 1A and 1B). Moreover, when tested on single cell suspensions obtained from either the tumor or the spleen of CT26 tumor-bearing mice, the aptamer library could discriminate TIMC from the splenic counterpart by preferentially recognizing MDSCs and macrophages from the tumor but not from the spleen of the same tumor-bearing animals or tumor-free mice (FIG. 1C).

Example 2—Identification of Four Monoclonal Aptamers Specific for Tumor-Infiltrating Myeloid Cells Monoclonal aptamers that can be easily produced and manipulated were identified using a bioinformatics pipeline. Briefly, polyclonal aptamer libraries from cycles 1, 6, 10, and 11 were HT-sequenced and data analyzed with APTANI, a computational tool to identify target-specific aptamers from HT-SELEX and secondary structure information (27). The analysis on the library from cycle 11 resulted in 154 monoclonal aptamers that showed an enrichment in the library higher than 0.01% and contained 158 secondary RNA motifs with a motif frequency higher than 0.05% of the total number of motifs. From this set of aptamers, we focused on 15 sequences that had an enrichment of at least 0.1% and contained either a large number of different secondary RNA motifs (i.e., at least 3 motifs) or at least 1 motif with a frequency higher than 0.1%. Interestingly, frequency analysis among cycles shows that most of these aptamers emerged starting from cycle 6, when stringency was gradually increased (data not shown).

Figure 2A:
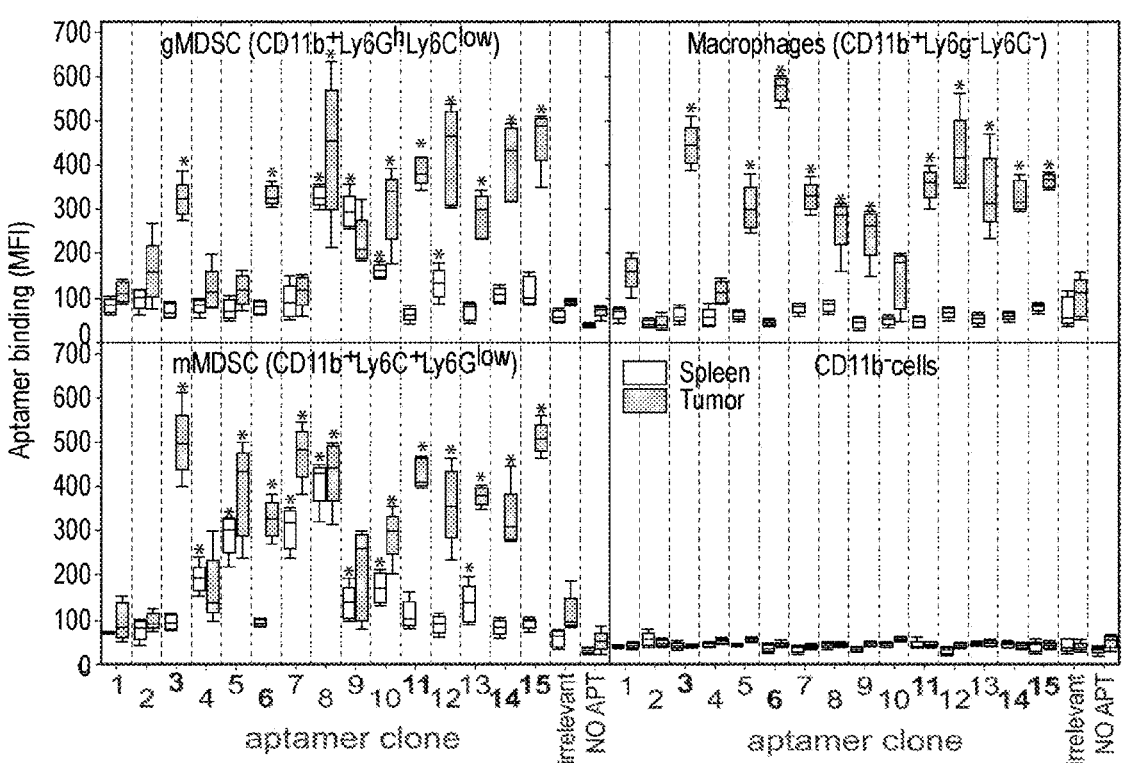
FIGS. 2A-C. Identification of monoclonal aptamers specific for tumor infiltrating myeloid cells.
Figure 2B:
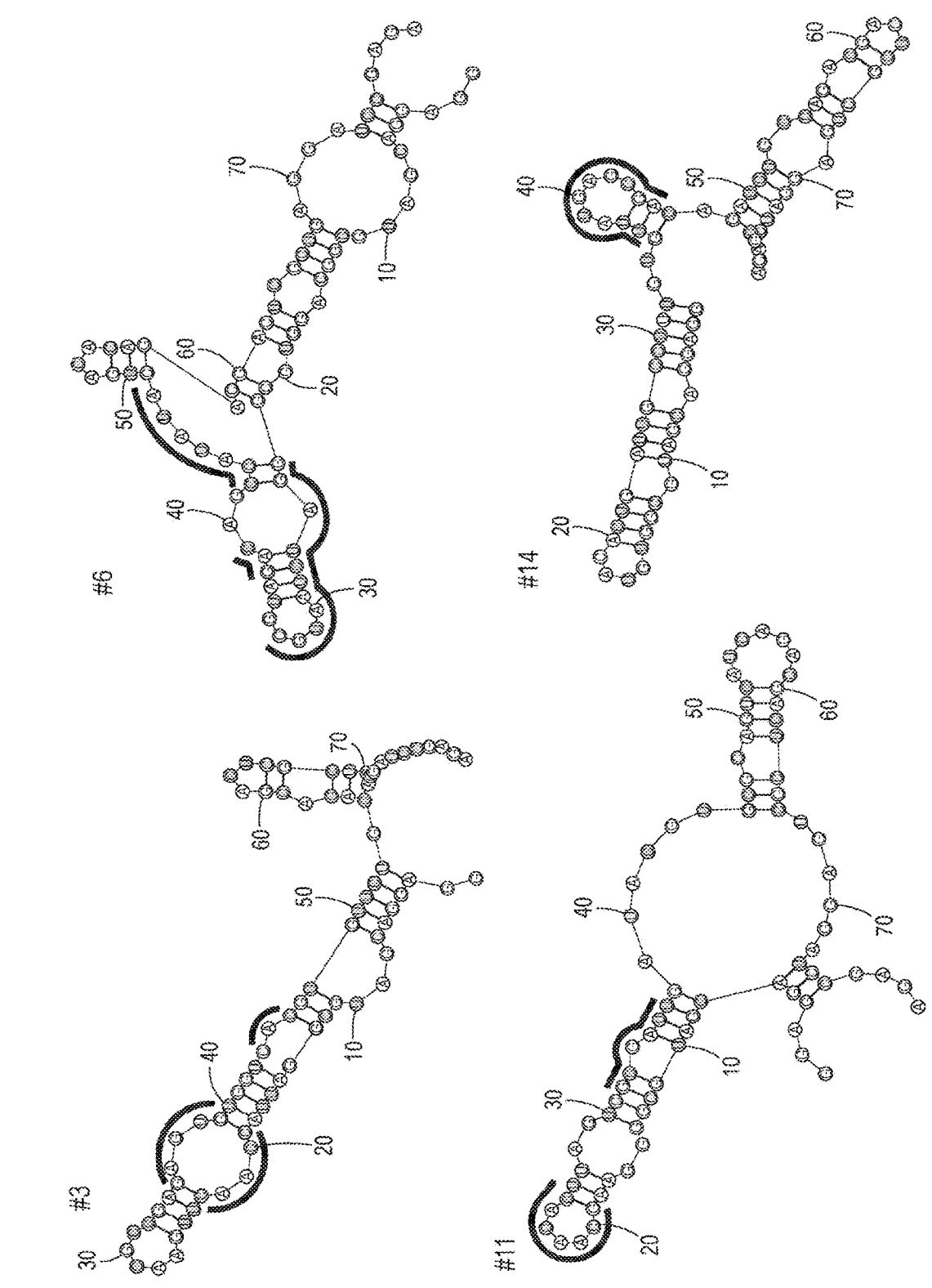

These 15 aptamers were tested by flow cytometry against single cell suspensions from tumor and spleen of mice challenged with the 4T1 tumor (FIG. 2A). While 12 out of 15 aptamers recognized macrophages, granulocytic MDSCs (gMDSC), and/or monocytic MDSCs (mMDSCs) from the tumor with statistically significant accuracy (as compared to an irrelevant aptamer; $p<0.001$; FIG. 1D), only 6 of them (i.e., apt 3, 6, 11, 12, 14, 15) were specific for tumor infiltrating myeloid cells and did not recognize any subset of splenic MDSCs nor CD11b-cells ($p>0.05$). Cluster and secondary structure analysis indicated that aptamers 15 and 11 were similar to aptamers 14 and 12, respectively (FIG. 9), thus only aptamer 3, 6, 11, and 14 (FIG. 2B) were chosen for further experiments.

Example 4—Aptamers 3, 6, 11 and 14 Recognize Tumor Infiltrating Myeloid Cells from Multiple Mouse Tumors The binding properties of monoclonal RNA aptamers 3, 6, 11 and 14 were evaluated in other tumor models. Aptamers 3, 6, 11, or 14 single cell suspensions were stained from tumor, bone marrow, spleen, and lungs of BALB/c mice bearing the 4T1 mammary carcinoma, the CT26 colon carcinoma, or the RENCA renal carcinoma. Similar analysis was performed on single cell suspensions from C57Bl/6 mice bearing B16LU8 melanoma, MCA203 fibrosarcoma or E0771 mammary carcinoma. The selected aptamers were able to recognize TIMC from all the tumors in both mice strains, whereas no or low staining was observed in myeloid cells from either the spleen or bone marrow, nor in the T and B cells. This finding indicates that, in all analyzed tumor samples, aptamer 3, 6, 11 and 14 were able to recognize TIMC, regardless of the mouse strain or tumor type. Interestingly, in different tumors, the selected aptamers recognize different tumor-infiltrating myeloid subsets.

Specificity was further evaluated by immunofluorescence microscopy using 4T1 tumors and tissues arrays from naïve mice. While all the selected aptamers recognized cells in the tumors most of the tissues appear to be negative for the aptamers with a few exceptions: aptamer 3 recognized hepatocytes at low intensity, aptamer 6 showed binding for epithelial cells in the uterus and low binding for pancreatic acinar tissue, and aptamer 14 recognized intestinal villi and seems to show a nuclear staining of cerebellum, pancreatic acinar tissue, stomach and spleen.

Figure 2C:
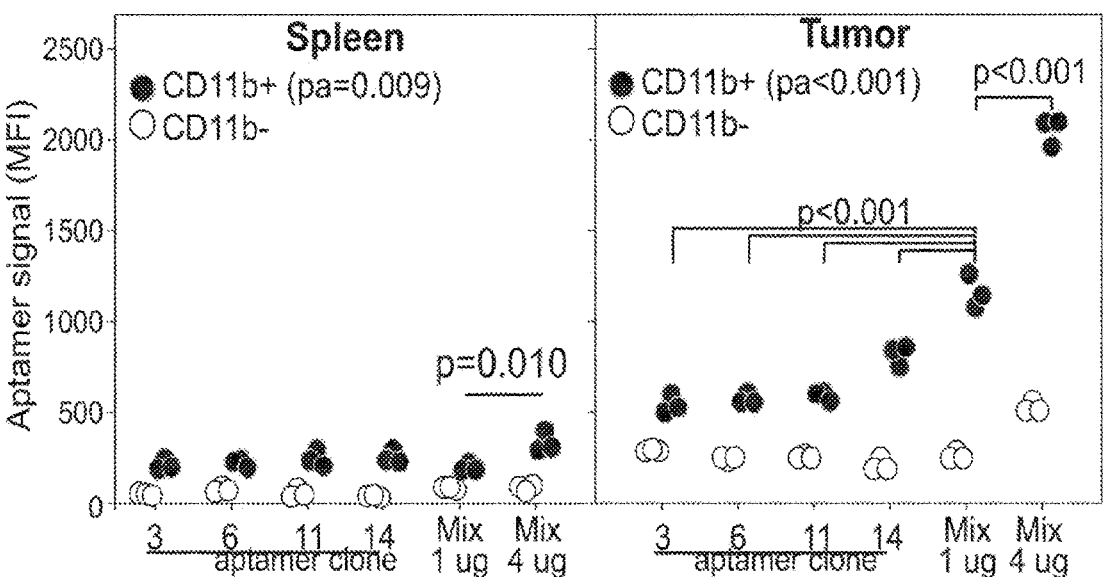

Next, whether an equimolar mixture of aptamers 3, 6, 11 and 14 was more efficient in recognizing TIMC as compared to each individual aptamer was evaluated. FACS analysis on cells from the spleen and from the tumor of 4T1 bearing mice revealed a clear additive/synergistic effect when using a mixture of the four aptamers (FIG. 2C).

The selected aptamers recognized human myeloid cells in the tumor but not in the blood of patients with Head and Neck Squamous Cell Carcinoma.

Figures 3A, 3B:
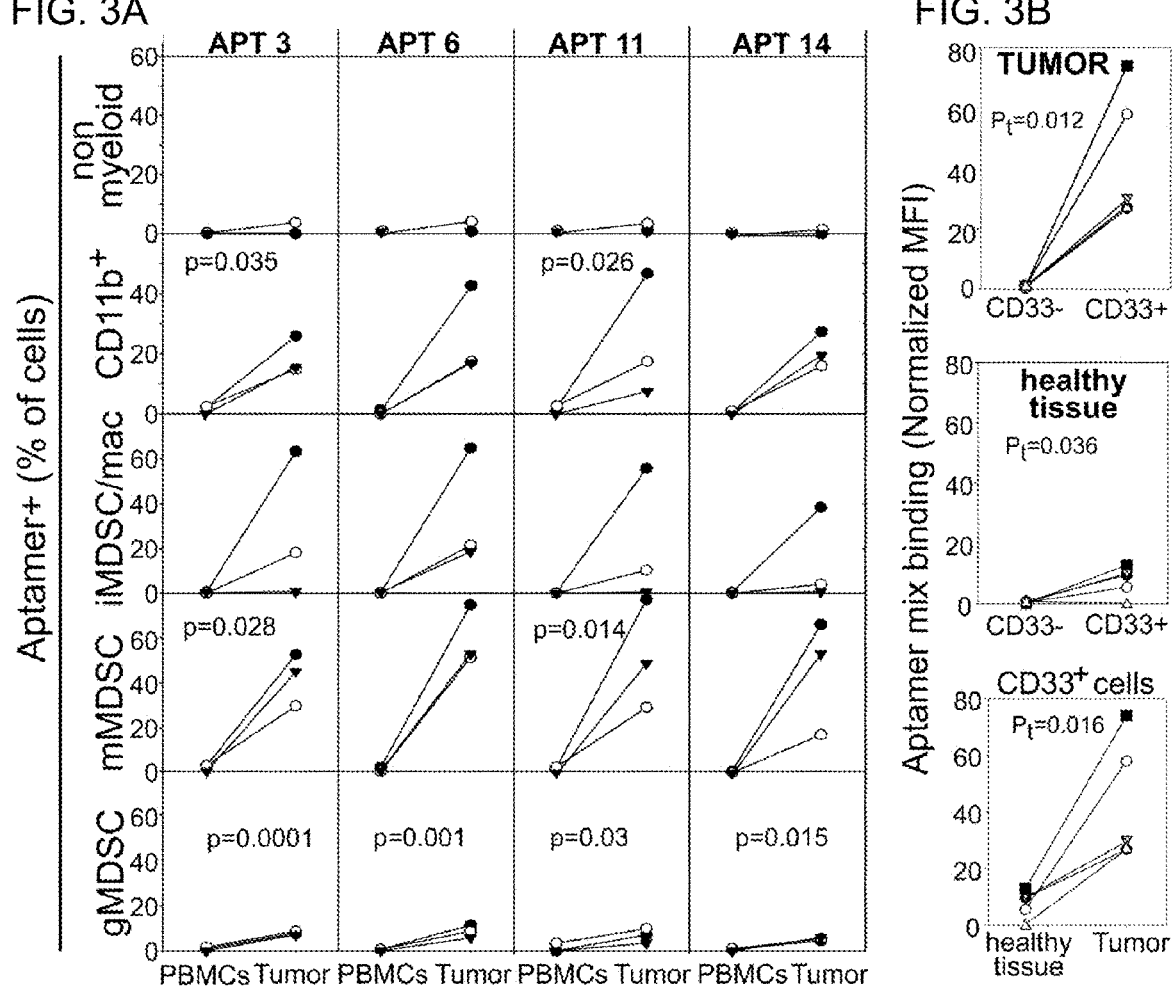
FIGS. 3A-3B. The selected RNA aptamers preferentially recognized human TIMC over the circulating myeloid cells from patients with recurrent HNSCC.

Having seen that the selected aptamers can discriminate between splenic and tumor infiltrating myeloid cells in mice, whether they could cross-react with human myeloid cells was tested and whether these aptamers could discriminate human TIMC from their circulating counterparts. Briefly, single cell suspension from the tumor or the blood of patients with recurrent HNSCC were stained with antibodies against CD33, HLADR, CD11b, CD14, CD15, and IL4Ra, counterstained with PE conjugated monoclonal aptamers and vital dye, and analyzed by flow cytometry (FIG. 3A). While no or low staining was detected in the PBMCs and in the non-myeloid cells, at least two aptamers recognized myeloid cells infiltrating the tumor from all the analyzed patients to different degrees. In particular, at the tumor site the selected aptamers recognize the majority of mMDSC and CD14-CD15-macrophages/iMDSC and a subset of gMDSC (FIG. 3A). Interestingly, within each subset, the aptamers recognize mostly the IL4Ra$^+$ cells that we have previously shown to be the suppressive myeloid cells and correlate with tumor recurrence in HNSCC (28).

Similar results were obtained by image cytometry. Briefly, paraffin-embedded tissue from patients with recurrent HNSCC were stained with an equimolar mixture of the 4 Cy3-labelled aptamers, and counter-stained with DAPI and anti-CD33 antibody. Images were acquired by a high-resolution scanner and data fed into cell profiler and FCS express for final analysis. Aptamers showed a higher binding on the CD33$^+$ cells infiltrating the tumor compared to the CD33$^-$ cells in the tumor and the CD33$^+$ cells present in the surrounding healthy tissue (FIG. 3B). Taken together, these data indicate that that the selected aptamers cross-react with human myeloid cells and recognize preferentially myeloid cells infiltrating HNSCC.

Example 4—Annexin A4 and Vimentin are the Putative Ligands for Aptamer 3 and 11

Aptamer-based immunoprecipitation and mass spectrometry identified annexin A4 (ANXA4 isoform X1 P97495) and vimentin (VIM P20152) as putative targets for aptamer 3 and 11, respectively (FIG. 4A). FACS analysis using beads loaded with relevant or irrelevant recombinant proteins confirmed the specificity of these two aptamers, for annexin and vimentin proteins and for IL4-treated MSC2 (FIGS. 4B and 4C). The specificity of aptamer 3 for ANXA4 and aptamer 11 for vimentin were tested by competitive experiments (FIG. 4D) and with validated shRNA (29) (FIG. 4E), respectively. No targets have been identified thus far for aptamers 6 and 14.

Example 5—Aptamers Specifically Recognize Tumor-Associated Myeloid Cells In Vivo To evaluate whether the aptamers can accumulate at the tumor site in vivo, mice orthotopically implanted with the 4T1-luciferase mammary carcinoma or tumor-free mice were treated intravenously with a mixture of aptamer 3, 6, 11 and 14 conjugated with Streptavidin-Alexa Fluor 750 or Alexa Fluor 647 (FIG. 5A). These fluorochromes allow detection of aptamer biodistribution by either in vivo imaging system (IVIS) or flow cytometry, respectively.

IVIS analysis revealed that the selected aptamers rapidly accumulate at the tumor site and in the liver (FIGS. 5B and 5C) and, subsequently, in the bladder. Signal from the TIMC-specific aptamers was detectable in the tumor 8 days after injection, whereas fluorescence signal in other tissues disappeared more rapidly indicating a preferential retention of the aptamers for the tumor microenvironment. Flow cytometry analysis (FIGS. 5D-5F) confirmed the IVIS results and indicated that aptamers in the tumor microenvironment preferentially bind to CD11b$^+$ myeloid cells (FIG. 5D), and in particular to mMDSC and TAM. Interestingly, time course analysis revealed that a population of aptamer-positive gMDSCs appears at later time points in the tumor and in the spleen of treated mice, (FIGS. 5E-5F), supporting previous evidence that mMDSCs can differentiate into gMDSCs (30, 31).

Example 6—TIMC-Specific Aptamers Maximize the Delivery of Doxorubicin at the Tumor Site Since TIMC-specific aptamers can target the tumor microenvironment, their drug delivery ability using doxorubicin (DOX) as chemotherapeutic agent was evaluated. Briefly, aptamers were extended in the 3' terminus with a GC rich tail that facilitate DOX intercalation (32, 33) and optimal loading conditions were evaluated by fluorescence spectroscopy (FIGS. 6A and 6B). To evaluate whether DOX-aptamer conjugates could target primary and metastatic lesions, an equimolar mixture of the four aptamers was loaded with DOX and injected intravenously into mice previously challenged with: i) 4T1 mammary carcinoma injected into the mammary gland (primary tumor in breast, metastasis in lung); ii) 4T1 administered intravenously (metastasis in the liver and lungs); or iii) the non-metastatic 4T1 variant 67NR injected into the mammary gland (no metastasis). Two hours after the injection, the bio-distribution of DOX-aptamer conjugates was evaluated by spectrophotometer analysis (FIG. 6C). The aptamers were able to deliver DOX to the primary mammary tumor and the metastatic sites. In mice with the non-metastatic 67NR tumor, DOX was found only in the affected breast tissue. In mice with the metastatic 4T1 injected intravenously, DOX was found in the liver and lungs (sites of metastatic cancer), whereas in mice with the 4T1 injected into the mammary gland, DOX accumulates at the primary tumor site and in the lung, a primary metastatic site in this model. Additional experiments indicated that DOX concentration at the tumor site of mice treated intravenously with 0.35 mg/kg ("low dose doxorubicin") of DOX-aptamer complexes was similar to those of mice treated with 3.5 mg/kg ("high dose") of free DOX, whereas in all other evaluated compartments the overall DOX concentration was significantly lower in the mice treated with DOX-aptamer complexes (FIG. 6D). These results not only indicate that doxorubicin conjugation does not affect the aptamer specificity but also that TIMC-specific aptamers can deliver chemotherapeutic agents to the primary and metastatic sites.

Example 7—TIMC-Specific Aptamers Increase Doxorubicin's Therapeutic Index

Next, the therapeutic efficacies of doxorubicin delivered by TIMC-specific aptamers was compared by PEGylated liposomes (Doxil, the first clinically available nanoparticle that became the gold standard for doxorubicin treatment (34, 35)), and as unconjugated molecules. Briefly, 4T1 bearing BALB/c mice were treated with unconjugated DOX at dose high, or low dose, or with low doses of DOX conjugated to the TIMC-specific aptamer, or with Doxil (low dose—0.35 mg/kg). Treatment was repeated 2 and 6 days later. As additional controls, mice were treated with unconjugated aptamers, irrelevant aptamers conjugated with doxorubicin, or left untreated. No significant anti-tumor effect was observed in mice treated with either high doses of free Doxorubicin or Doxil (FIG. 7A). Conversely, low doses of doxorubicin delivered via TIMC-specific aptamer significantly delayed tumor progression and resulted in 40% of treated mice being without a clinically detectable tumor 60 days after treatment (FIG. 7A). Furthermore, while high doses of free doxorubicin resulted in high toxicity, as determined by significant body weight loss and 15% treatment related mortality, no toxicity was observed with DOX-loaded aptamer (FIG. 7B).

Since depletion or inactivation of MDSCs can delay tumor progression (19) and doxorubicin has reportedly depleted (36) MDSCs or impaired their function (37), we asked whether the observed anti-tumor efficacy was due to the bystander release of doxorubicin in the tumor microenvironment or rather the depletion/inactivation of MDSCs. To this aim, we evaluated the efficacy of treatment using a doxorubicin resistant 4T1 cell line (DoxR-4T1) and the doxorubicin sensitive parental cell line. DOX-loaded aptamer treatment confirmed its efficacy on the doxorubicin sensitive parental cell line, whereas no therapeutic effect was observed in mice challenged with the doxorubicin resistant 4T1 tumor (FIG. 7C).

Example 8—Aptamer Effectively Deliver CCR1 and 5 siRNA to Tumor Infiltrating Myeloid Cells and Delay Tumor Progression Balb/c mice were challenged orthotopically with the 4T1 mammary carcinoma and treated intravenously with a mixture of aptamers 3, 6, 11 and 14 each loaded with a) scrambled siRNAs (black bar) or with siRNAs against CCR1 and CCR5 (30 picomoles, empty bar) 5, 7, 9, 12, 14, 16 and 19 days after the challenge. qRT-PCR for CCR1 and CCR5 mRNA was performed 6 days after the last treatment on magnetically isolated tumor infiltrating myeloid cells from each group. Results show that the aptamers' mixture effectively deliver the siRNAs against CCR1 and CCR5 allowing the in vivo silencing of both genes whereas no effect were seen with the scrambled siRNAs controls (data not shown). Importantly, the aptamer mediated delivery of both siRNA into the tumor infiltrating myeloid cells induced a significant reduction of tumor size (data not shown). Taken together, these results indicate that aptamers can deliver therapeutic siRNAs in vivo into tumor infiltrating myeloid cells and affect tumor progression.

REFERENCES

1. C. Carvalho, R. X. Santos, S. Cardoso, S. Correia, P. J. Oliveira, M. S. Santos, P. I. Moreira, Doxorubicin: the good, the bad and the ugly effect. Current medicinal chemistry 16, 3267-3285 (2009).
2. J. Kydd, R. Jadia, P. Velpurisiva, A. Gad, S. Paliwal, P. Rai, Targeting Strategies for the Combination Treatment of Cancer Using Drug Delivery Systems. Pharmaceutics 9, (2017).
3. C. Kinnear, T. L. Moore, L. Rodriguez-Lorenzo, B. Rothen-Rutishauser, A. Petri-Fink, Form Follows Function: Nanoparticle Shape and Its Implications for Nanomedicine. Chemical reviews 117, 11476-11521 (2017).
4. B. Bahrami, M. Hojjat-Farsangi, H. Mohammadi, E. Anvari, G. Ghalamfarsa, M. Yousefi, F. Jadidi-Niaragh, Nanoparticles and targeted drug delivery in cancer therapy. Immunology letters 190, 64-83 (2017).
5. P. Tiet, J. M. Berlin, Exploiting homing abilities of cell carriers: Targeted delivery of nanoparticles for cancer therapy. Biochemical pharmacology, (2017).
6. U. Prabhakar, H. Maeda, R. K. Jain, E. M. Sevick-Muraca, W. Zamboni, O. C. Farokhzad, S. T. Barry, A. Gabizon, P. Grodzinski, D. C. Blakey, Challenges and key considerations of the enhanced permeability and retention (EPR) effect for nanomedicine drug delivery in oncology. Cancer research 73, 2412-2417 (2013).
7. M. Ruella, D. M. Barrett, S. S. Kenderian, O. Shestova, T. J. Hofmann, J. Scholler, S. F. Lacey, J. J. Melenhorst, F. Nazimuddin, J. Perazzelli, D. A. Christian, C. A. Hunter, D. L. Porter, C. H. June, S. A. Grupp, S. Gill, Treatment of leukemia antigen-loss relapses occurring after CD19-targeted immunotherapies by combination of anti-CD123 and anti-CD19 chimeric antigen receptor T cells. Journal for Immunotherapy of Cancer 3, O5-O5 (2015).
8. S. Kelderman, T. N. M. Schumacher, J. B. A. G. Haanen, Acquired and intrinsic resistance in cancer immunotherapy. Molecular Oncology 8, 1132-1139 (2014).
9. H. Attarwala, Role of antibodies in cancer targeting. Journal of Natural Science, Biology, and Medicine 1, 53-56 (2010).
10. C. Szot, S. Saha, X. M. Zhang, Z. Zhu, M. B. Hilton, K. Morris, S. Seaman, J. M. Dunleavey, K.-S. Hsu, G.-J. Yu, H. Morris, D. A. Swing, D. C. Haines, Y. Wang, J. Hwang, Y. Feng, D. Welsch, G. DeCrescenzo, A. Chaudhary, E. Zudaire, D. S. Dimitrov, B. St. Croix, Tumor stroma-targeted antibody-drug conjugate triggers localized anticancer drug release. The Journal of Clinical Investigation 128, 2927-2943 (2018).
11. T. Condamine, I. Ramachandran, J. I. Youn, D. I. Gabrilovich, Regulation of tumor metastasis by myeloid-derived suppressor cells. Annu Rev Med 66, 97-110 (2015).

12. D. Marvel, D. I. Gabrilovich, Myeloid-derived suppressor cells in the tumor microenvironment: expect the unexpected. J Clin Invest 125, 3356-3364 (2015).

13. A. Arina, L. Corrales, V. Bronte, Enhancing T cell therapy by overcoming the immunosuppressive tumor microenvironment. Semin Immunol, (2016).

14. S. Ugel, F. De Sanctis, S. Mandruzzato, V. Bronte, Tumor-induced myeloid deviation: when myeloid-derived suppressor cells meet tumor-associated macrophages. J Clin Invest 125, 3365-3376 (2015).

15. S. Zilio, P. Serafini, Neutrophils and Granulocytic MDSC: The Janus God of Cancer Immunotherapy. Vaccines 4, (2016).

16. P. Serafini, Myeloid derived suppressor cells in physiological and pathological conditions: the good, the bad, and the ugly. Immunol Res 57, 172-184 (2013).

17. T. Kitamura, B.-Z. Qian, J. W. Pollard, Immune cell promotion of metastasis. 15, 73 (2015).

18. B. R. Achyut, A. S. Arbab, Myeloid cell signatures in tumor microenvironment predicts therapeutic response in cancer. OncoTargets and therapy 9, 1047-1055 (2016).

19. S. Ugel, F. De Sanctis, S. Mandruzzato, V. Bronte, Tumor-induced myeloid deviation: when myeloid-derived suppressor cells meet tumor-associated macrophages. The Journal of Clinical Investigation 125, 3365-3376 (2015).

20. S. Kusmartsev, D. I. Gabrilovich, STAT1 signaling regulates tumor-associated macrophage-mediated T cell deletion. J Immunol 174, 4880-4891 (2005).

21. V. Kumar, S. Patel, E. Tcyganov, D. I. Gabrilovich, The nature of myeloid-derived suppressor cells in the tumor microenvironment. Trends in immunology 37, 208-220 (2016).

22. A. A. Al-Khami, L. Zheng, L. Del Valle, F. Hossain, D. Wyczechowska, J. Zabaleta, M. D. Sanchez, M. J. Dean, P. C. Rodriguez, A. C. Ochoa, Exogenous lipid uptake induces metabolic and functional reprogramming of tumor-associated myeloid-derived suppressor cells. OncoImmunology 6, e1344804 (2017).

23. S. Catuogno, C. L. Esposito, Aptamer Cell-Based Selection: Overview and Advances. Biomedicines 5, (2017).

24. J. Zhou, J. Rossi, Aptamers as targeted therapeutics: current potential and challenges. Nature reviews. Drug discovery 16, 181-202 (2017).

25. M. Hamada, In silico approaches to RNA aptamer design. Biochimie, (2017).

26. E. Apolloni, V. Bronte, A. Mazzoni, P. Serafini, A. Cabrelle, D. M. Segal, H. A. Young, P. Zanovello, Immortalized myeloid suppressor cells trigger apoptosis in antigen-activated T lymphocytes. J Immunol 165, 6723-6730 (2000).

27. J. *Caroli*, C. Taccioli, A. De La Fuente, P. Serafini, S. Bicciato, APTANI: a computational tool to select aptamers through sequence-structure motif analysis of HT-SELEX data. Bioinformatics 32, 161-164 (2016).

28. D. T. Weed, J. L. Vella, I. M. Reis, A. C. De la Fuente, C. Gomez, Z. Sargi, R. Nazarian, J. Califano, I. Borrello, P. Serafini, Tadalafil reduces myeloid-derived suppressor cells and regulatory T cells and promotes tumor immunity in patients with head and neck squamous cell carcinoma. Clin Cancer Res 21, 39-48 (2015).

29. M. Desclaux, M. Teigell, L. Amar, R. Vogel, Y. R. M. Gimenez, A. Privat, J. Mallet, A novel and efficient gene transfer strategy reduces glial reactivity and improves neuronal survival and axonal growth in vitro. PLoS One 4, e6227 (2009).

30. S. Zilio, J. L. Vella, A. C. De la Fuente, P. M. Daftarian, D. T. Weed, A. Kaifer, I. Marigo, K. Leone, V. Bronte, P. Serafini, 4PD Functionalized Dendrimers: A Flexible Tool for In Vivo Gene Silencing of Tumor-Educated Myeloid Cells. J Immunol 198, 4166-4177 (2017).

31. J.-I. Youn, V. Kumar, M. Collazo, Y. Nefedova, T. Condamine, P. Cheng, A. Villagra, S. Antonia, J. C. McCaffrey, M. Fishman, A. Sarnaik, P. Horna, E. Sotomayor, D. I. Gabrilovich, Epigenetic silencing of retinoblastoma gene regulates pathologic differentiation of myeloid cells in cancer. Nature immunology 14, 211-220 (2013).

32. C. H. Stuart, D. A. Horita, M. J. Thomas, F. R. Salsbury, M. O. Lively, W. H. Gmeiner, Site-Specific DNA-Doxorubicin Conjugates Display Enhanced Cytotoxicity to Breast Cancer Cells. Bioconjugate Chemistry 25, 406-413 (2014).

33. V. Bagalkot, O. C. Farokhzad, R. Langer, S. Jon, An aptamer-doxorubicin physical conjugate as a novel targeted drug-delivery platform. Angew Chem Int Ed Engl 45, 8149-8152 (2006).

34. S. M. Rafiyath, M. Rasul, B. Lee, G. Wei, G. Lamba, D. Liu, Comparison of safety and toxicity of liposomal doxorubicin vs. conventional anthracyclines: a meta-analysis. Experimental Hematology & Oncology 1, 10 (2012).

35. U. Bulbake, S. Doppalapudi, N. Kommineni, W. Khan, Liposomal Formulations in Clinical Use: An Updated Review. Pharmaceutics 9, 12 (2017).

36. N. N. Belyaev, N. Abdolla, Y. V. Perfilyeva, Y. O. Ostapchuk, V. K. Krasnoshtanov, A. Kali, R. Tleulieva, Daunorubicin conjugated with alpha-fetoprotein selectively eliminates myeloid-derived suppressor cells (MDSCs) and inhibits experimental tumor growth. Cancer immunology, immunotherapy: CII 67, 101-111 (2018).

37. D. Alizadeh, M. Trad, N. T. Hanke, C. B. Larmonier, N. Janikashvili, B. Bonnotte, E. Katsanis, N. Larmonier, Doxorubicin eliminates myeloid-derived suppressor cells and enhances the efficacy of adoptive T-cell transfer in breast cancer. Cancer Res 74, 104-118 (2014).

38. L. Ansari, F. Shiehzadeh, Z. Taherzadeh, S. Nikoofal-Sahlabadi, A. A. Momtazi-Borojeni, A. Sahebkar, S. Eslami, The most prevalent side effects of pegylated liposomal doxorubicin monotherapy in women with metastatic breast cancer: a systematic review of clinical trials. Cancer gene therapy 24, 189-193 (2017).

39. A. Sica, V. Bronte, Altered macrophage differentiation and immune dysfunction in tumor development. J Clin Invest 117, 1155-1166 (2007).

40. N. Erez, L. M. Coussens, Leukocytes as paracrine regulators of metastasis and determinants of organ-specific colonization. Int J Cancer 128, 2536-2544 (2011).

41. J. W. Pollard, Tumour-educated macrophages promote tumour progression and metastasis. Nat Rev Cancer 4, 71-78 (2004).

42. C. Steidl, T. Lee, S. P. Shah, P. Farinha, G. Han, T. Nayar, A. Delaney, S. J. Jones, J. Iqbal, D. D. Weisenburger, M. A. Bast, A. Rosenwald, H. K. Muller-Hermelink, L. M. Rimsza, E. Campo, J. Delabie, R. M. Braziel, J. R. Cook, R. R. Tubbs, E. S. Jaffe, G. Lenz, J. M. Connors, L. M. Staudt, W. C. Chan, R. D. Gascoyne, Tumor-associated macrophages and survival in classic Hodgkin's lymphoma. N Engl J Med 362, 875-885 (2010).

43. J. Zhang, L. Patel, K. J. Pienta, CC chemokine ligand 2 (CCL2) promotes prostate cancer tumorigenesis and metastasis. Cytokine Growth Factor Rev 21, 41-48 (2010).

44. G. Gallina, L. Dolcetti, P. Serafini, C. De Santo, I. Marigo, M. P. Colombo, G. Basso, F. Brombacher, I. Borrello, P. Zanovello, S. Bicciato, V. Bronte, Tumors induce a subset of inflammatory monocytes with immunosuppressive activity on CD8+ T cells. J Clin Invest 116, 2777-2790 (2006).

45. S. Kusmartsev, S. Nagaraj, D. I. Gabrilovich, Tumor-associated CD8+ T cell tolerance induced by bone marrow-derived immature myeloid cells. J Immunol 175, 4583-4592 (2005).

46. V. Fleming, X. Hu, R. Weber, V. Nagibin, C. Groth, P. Altevogt, J. Utikal, V. Umansky, Targeting Myeloid-Derived Suppressor Cells to Bypass Tumor-Induced Immunosuppression. Frontiers in immunology 9, 398 (2018).

47. S. Hamada, A. Masamune, T. Shimosegawa, Novel therapeutic strategies targeting tumor-stromal interactions in pancreatic cancer. Frontiers in physiology 4, 331 (2013).

48. F. Veglia, M. Perego, D. Gabrilovich, Myeloid-derived suppressor cells coming of age. Nat Immunol 19, 108-119 (2018).

49. H. Liu, J. Mai, J. Shen, J. Wolfram, Z. Li, G. Zhang, R. Xu, Y. Li, C. Mu, Y. Zu, X. Li, G. L. Lokesh, V. Thiviyanathan, D. E. Volk, D. G. Gorenstein, M. Ferrari, Z. Hu, H. Shen, A Novel DNA Aptamer for Dual Targeting of Polymorphonuclear Myeloid-derived Suppressor Cells and Tumor Cells. Theranostics 8, 31-44 (2018).

50. H. Qin, B. Lerman, I. Sakamaki, G. Wei, S. C. Cha, S. S. Rao, J. Qian, Y. Hailemichael, R. Nurieva, K. C. Dwyer, J. Roth, Q. Yi, W. W. Overwijk, L. W. Kwak, Generation of a new therapeutic peptide that depletes myeloid-derived suppressor cells in tumor-bearing mice. Nature medicine 20, 676-681 (2014).

51. F. Roth, A. C. De La Fuente, J. L. Vella, A. Zoso, L. Inverardi, P. Serafini, Aptamer-Mediated Blockade of IL4Ralpha Triggers Apoptosis of MDSCs and Limits Tumor Progression. Cancer Res 72, 1373-1383 (2012).

52. S. Bilalic, A. Michlmayr, V. Gruber, E. Buchberger, C. Burghuber, G. A. Bohmig, R. Oehler, Lymphocyte activation induces cell surface expression of an immunogenic vimentin isoform. Transplant immunology 27, 101-106 (2012).

53. A. Mitra, A. Satelli, X. Xia, J. Cutrera, L. Mishra, S. Li, Cell-surface Vimentin: A mislocalized protein for isolating csVimentin(+) CD133(−) novel stem-like hepatocellular carcinoma cells expressing EMT markers. International journal of cancer 137, 491-496 (2015).

54. N. Mor-Vaknin, A. Punturieri, K. Sitwala, D. M. Markovitz, Vimentin is secreted by activated macrophages. Nat Cell Biol 5, 59-63 (2003).

55. P. Benes, V. Maceckova, Z. Zdrahal, H. Konecna, E. Zahradnickova, J. Muzik, J. Smarda, Role of vimentin in regulation of monocyte/macrophage differentiation. Differentiation 74, 265-276 (2006).

56. Y. Lou, O. Preobrazhenska, U. auf dem Keller, M. Sutcliffe, L. Barclay, P. C. McDonald, C. Roskelley, C. M. Overall, S. Dedhar, Epithelial-mesenchymal transition (EMT) is not sufficient for spontaneous murine breast cancer metastasis. Dev Dyn 237, 2755-2768 (2008).

57. T. R. Sarkar, V. L. Battula, S. J. Werden, G. V. Vijay, E. Q. Ramirez-Pena, J. H. Taube, J. T. Chang, N. Miura, W. Porter, N. Sphyris, M. Andreeff, S. A. Mani, GD3 synthase regulates epithelial-mesenchymal transition and metastasis in breast cancer. Oncogene 34, 2958-2967 (2015).

58. T. L. Boye, K. Maeda, W. Pezeshkian, S. L. Sonder, S. C. Haeger, V. Gerke, A. C. Simonsen, J. Nylandsted, Annexin A4 and A6 induce membrane curvature and constriction during cell membrane repair. Nature Communications 8, 1623 (2017).

59. F. O. Martinez, L. Helming, R. Milde, A. Varin, B. N. Melgert, C. Draijer, B. Thomas, M. Fabbri, A. Crawshaw, L. P. Ho, N. H. Ten Hacken, V. Cobos Jimenez, N. A. Kootstra, J. Hamann, D. R. Greaves, M. Locati, A. Mantovani, S. Gordon, Genetic programs expressed in resting and IL-4 alternatively activated mouse and human macrophages: similarities and differences. Blood 121, e57-69 (2013).

60. M. Diakonova, V. Gerke, J. Ernst, J. P. Liautard, G. van der Vusse, G. Griffiths, Localization of five annexins in J774 macrophages and on isolated phagosomes. Journal of Cell Science 110, 1199-1213 (1997).

61. F. O. Martinez, L. Helming, R. Milde, A. Varin, B. N. Melgert, C. Draijer, B. Thomas, M. Fabbri, A. Crawshaw, L. P. Ho, N. H. Ten Hacken, V. Cobos Jiménez, N. A. Kootstra, J. Hamann, D. R. Greaves, M. Locati, A. Mantovani, S. Gordon, Genetic programs expressed in resting and IL-4 alternatively activated mouse and human macrophages: similarities and differences. Blood 121, e57-e69 (2013).

62. B. A. Pulaski, S. Ostrand-Rosenberg, Mouse 4T1 breast tumor model. Current protocols in immunology Chapter 20, Unit 20.22 (2001).

63. P. Serafini, K. Meckel, M. Kelso, K. Noonan, J. Califano, W. Koch, L. Dolcetti, V. Bronte, I. Borrello, Phosphodi-esterase-5 inhibition augments endogenous antitumor immunity by reducing myeloid-derived suppressor cell function. J Exp Med 203, 2691-2702 (2006).

64. P. Nanni, C. de Giovanni, P. L. Lollini, G. Nicoletti, G. Prodi, TS/A: a new metastasizing cell line from a BALB/c spontaneous mammary adenocarcinoma. Clinical & experimental metastasis 1, 373-380 (1983).

65. M. G. Brattain, J. Strobel-Stevens, D. Fine, M. Webb, A. M. Sarrif, Establishment of mouse colonic carcinoma cell lines with different metastatic properties. Cancer Res 40, 2142-2146 (1980).

66. G. P. Murphy, W. J. Hrushesky, A murine renal cell carcinoma. Journal of the National Cancer Institute 50, 1013-1025 (1973).

67. R. J. Barth, S. N. Bock, J. J. Mul6, S. A. Rosenberg, Unique murine tumor-associated antigens identified by tumor infiltrating lymphocytes. The Journal of Immunology 144, 1531-1537 (1990).

68. C. J. Aslakson, F. R. Miller, Selective events in the metastatic process defined by analysis of the sequential dissemination of subpopulations of a mouse mammary tumor. Cancer Res 52, 1399-1405 (1992).

69. J. M. Layzer, B. A. Sullenger, Simultaneous generation of aptamers to multiple gamma-carboxyglutamic acid proteins from a focused aptamer library using DeSELEX and convergent selection. Oligonucleotides 17, 1-11 (2007).

70. M. Ahmed, W. E. Monsky, G. Girnun, A. Lukyanov, G. D'Ippolito, J. B. Kruskal, K. E. Stuart, V. P. Torchilin, S. N. Goldberg, Radiofrequency thermal ablation sharply increases intratumoral liposomal doxorubicin accumulation and tumor coagulation. Cancer Res 63, 6327-6333 (2003).

What is claimed is:

1. An RNA aptamer comprising the nucleic acid sequence set forth in any one of SEQ ID NOs: 3, 6, 11, 12, 14, and 15 conjugated to a chemotherapeutic agent or a nucleic acid molecule.

2. The aptamer of claim 1, wherein the nucleic acid molecule is DNA, RNA, shRNA, siRNA or miRNA.

3. The aptamer of claim 1, wherein the chemotherapeutic agent is doxorubicin.

4. A method of delivering a therapeutic to a tumor-infiltrating myeloid cell comprising contacting the cell with the aptamer of claim 1, wherein the therapeutic is a chemotherapeutic agent or a nucleic acid molecule.

5. A method of detecting the presence of a tumor-infiltrating myeloid cell in a biological sample, comprising contacting the sample with the aptamer of claim 1 conjugated to a detectable label.

* * * * *

SEQUENCE LISTING

<160> NUMBER OF SEQ ID NOS: 53

<210> SEQ ID NO 1
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 1
ggaggacgau gcggccuagu acacaagauc ugacaccucg auacagauau gaggcagacg      60
acucgcugag gauccgaga                                                   79

<210> SEQ ID NO 2
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 2
ggaggacgau gcggccuagu acaaaagccu gaucucugug agcagacacu agaacagacg      60
acucgcugag gauccgaga                                                   79

<210> SEQ ID NO 3
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 3
ggaggacgau gcggauuacc aacuugaacg ccgagagugu ggucacgugu ucugcagacg      60
acucgcugag gauccgaga                                                   79

<210> SEQ ID NO 4
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 4
ggaggacgau gcggcaacaa acuaaucaga cacgagacag agagauagau cugacagacg      60
acucgcugag gauccgaga                                                   79

<210> SEQ ID NO 5
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 5
ggaggacgau gcggccggag gcagucacua aucuucacuu cucucagaca ugcgcagacg      60
acucgcugag gauccgaga                                                   79

<210> SEQ ID NO 6
<211> LENGTH: 79
<212> TYPE: DNA
<213> ORGANISM: Artificial Sequence
<220> FEATURE:
<223> OTHER INFORMATION: Synthetic Oligonucleotide -continued

<400> SEQUENCE: 6
ggaggacgau gcggcaggug cgggaucuaa ugcguagaca gccauauacu gacacagacg      60
acucgcugag gauccgaga                                                   79

<210> SEQ ID NO 7
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 7
ggaggacgau gcggacgacg uuuacugacc acgauauguc agauucgguc cucaucagac      60
gacucgcuga ggauccgaga                                                  80

<210> SEQ ID NO 8
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 8
ggaggacgau gcggcauaca cacuugacuc uagagaacga gcaucuagcg guguccagac      60
gacucgcuga ggauccgaga                                                  80

<210> SEQ ID NO 9
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 9
ggaggacgau gcgggugacu aggcaagcac aaaacugucg cucaugacag aucugucaga      60
cgacucgcug aggauccgag a                                                81

<210> SEQ ID NO 10
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 10
ggaggacgau gcggacggag gauaguugcu aaucgagcgc ugccgacgcu ccagacgacu      60
cgcugaggau ccgaga                                                      76

<210> SEQ ID NO 11
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 11
ggaggacgau gcggggaagc aacacuuagu cgcgauugau acgugcgcag ucaucagacg      60
acucgcugag gauccgaga                                                   79

<210> SEQ ID NO 12

-continued

<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 12
ggaggacgau gcggggaagc aacacuuagu cgcgauugau acgugcgcag ucagcagacg        60
acucgcugag gauccgaga                                                     79

<210> SEQ ID NO 13
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 13
ggaggacgau gcggacggag gauaguugcu aaucgagcgc ugcgcacgcu ccagacgacu        60
cgcugaggau ccgaga                                                        76

<210> SEQ ID NO 14
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 14
ggaggacgau gcgguguaca cugauugccu uuguguuaug agcgacagau cugccagacg        60
acucgcugag gauccgaga                                                     79

<210> SEQ ID NO 15
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 15
ggaggacgau gcgguguaca cugauugccu cuguguuaug agcgacagau cugccagacg        60
acucgcugag gauccgaga                                                     79

<210> SEQ ID NO 16
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 16
tctcggatcc tcagcgagtc gtctg                                              25

<210> SEQ ID NO 17
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 17
ccgcatcgtc ctccta                                                        17

-continued

```
<210> SEQ ID NO 18
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 18
tctcggatcc tcagcgagtc gtc                                                  23

<210> SEQ ID NO 19
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 19
gggggaattc taatacgact cactataggg aggacgatgc gg                             42

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
tctcggatcc tcagcgagtc                                                      20

<210> SEQ ID NO 21
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 21
atcgatcgat cgatcgatcg atcgatcgat ttttcgatcg atcgatcgac tgatcgatcg         60
tctcggatcc tcagcgagtc gtc                                                  83

<210> SEQ ID NO 22
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 22
tagggaggac gatgcggcct agtacacaag atctgacacc tcgatacaga tatgaggcag         60
acgactcgct gaggatccga ga                                                   82

<210> SEQ ID NO 23
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 23
tagggaggac gatgcggcct agtacaaaag cctgatctct gtgagcagac actagaacag         60
acgactcgct gaggatccga ga                                                   82

<210> SEQ ID NO 24
```

```
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 24
tagggaggac gatgcggatt accaacttga acgccgagag tgtggtcacg tgttctgcag        60
acgactcgct gaggatccga ga                                                 82

<210> SEQ ID NO 25
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 25
tagggaggac gatgcggcaa caaactaatc agacacgaga cagagagata gatctgacag        60
acgactcgct gaggatccga ga                                                 82

<210> SEQ ID NO 26
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 26
tagggaggac gatgcggccg gaggcagtca ctaatcttca cttctctcag acatgcgcag        60
acgactcgct gaggatccga ga                                                 82

<210> SEQ ID NO 27
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 27
tagggaggac gatgcggcag gtgcgggatc taatgcgtag acagccatat actgacacag        60
acgactcgct gaggatccga ga                                                 82

<210> SEQ ID NO 28
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 28
tagggaggac gatgcggacg acgtttactg accacgatat gtcagattcg gtcctcatca        60
gacgactcgc tgaggatccg aga                                                83

<210> SEQ ID NO 29
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 29
tagggaggac gatgcggcat acacacttga ctctagagaa cgagcatcta gcggtgtcca        60
```

-continued

```
gacgactcgc tgaggatccg aga                                              83

<210> SEQ ID NO 30
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 30
tagggaggac gatgcgggtg actaggcaag cacaaaactg tcgctcatga cagatctgtc    60
agacgactcg ctgaggatcc gaga                                            84

<210> SEQ ID NO 31
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 31
tagggaggac gatgcggacg gaggatagtt gctaatcgag cgctgccgac gctccagacg    60
actcgctgag gatccgaga                                                  79

<210> SEQ ID NO 32
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 32
tagggaggac gatgcgggga agcaacactt agtcgcgatt gatacgtgcg cagtcatcag    60
acgactcgct gaggatccga ga                                              82

<210> SEQ ID NO 33
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 33
tagggaggac gatgcgggga agcaacactt agtcgcgatt gatacgtgcg cagtcagcag    60
acgactcgct gaggatccga ga                                              82

<210> SEQ ID NO 34
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 34
tagggaggac gatgcggacg gaggatagtt gctaatcgag cgctgcgcac gctccagacg    60
actcgctgag gatccgaga                                                  79

<210> SEQ ID NO 35
<211> LENGTH: 82
<212> TYPE: DNA
<213> ORGANISM: Artificial Sequence
<220> FEATURE:
```

-continued

```
<223> OTHER INFORMATION: Synthetic Oligonucleotide

<400> SEQUENCE: 35
tagggaggac gatgcggtgt acactgattg cctttgtgtt atgagcgaca gatctgccag      60
acgactcgct gaggatccga ga                                              82

<210> SEQ ID NO 36
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 36
tagggaggac gatgcggtgt acactgattg cctctgtgtt atgagcgaca gatctgccag      60
acgactcgct gaggatccga ga                                              82

<210> SEQ ID NO 37
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 37
acactctttc cctacacgac gctcttccga tctctagtga ggacgatgcg g              51

<210> SEQ ID NO 38
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 38
acactctttc cctacacgac gctcttccga tctagctgga ggacgatgcg g              51

<210> SEQ ID NO 39
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 39
acactctttc cctacacgac gctcttccga tcttcgacga ggacgatgcg g              51

<210> SEQ ID NO 40
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 40
acactctttc cctacacgac gctcttccga tctgatcaga ggacgatgcg g              51

<210> SEQ ID NO 41
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 41
```

-continued

```
aatgatacgg cgaccaccga gatctacact ctttccctac acgacgctct tccgatct          58

<210> SEQ ID NO 42
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 42
atctcgtatg ccgtcttctg cttgtctcgg atcctcagcg agtc                         44

<210> SEQ ID NO 43
<211> LENGTH: 63
<212> TYPE: DNA
<213> ORGANISM: Artificial Sequence
<220> FEATURE:
<223> OTHER INFORMATION: Synthetic Oligonucleotide

<400> SEQUENCE: 43
gatcggaaga gcacacgtct gaactccagt caccgatgta tctcgtatgc cgtcttctgc        60
ttg                                                                      63

<210> SEQ ID NO 44
<211> LENGTH: 63
<212> TYPE: DNA
<213> ORGANISM: Artificial Sequence
<220> FEATURE:
<223> OTHER INFORMATION: Synthetic Oligonucleotide

<400> SEQUENCE: 44
gatcggaaga gcacacgtct gaactccagt cacatcacga tctcgtatgc cgtcttctgc        60
ttg                                                                      63

<210> SEQ ID NO 45
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 45
gatcggaaga gcacacgtct gaactccagt cactgaccaa tctcgtatgc cgtcttctgc        60
t                                                                        61

<210> SEQ ID NO 46
<211> LENGTH: 63
<212> TYPE: DNA
<213> ORGANISM: Artificial Sequence
<220> FEATURE:
<223> OTHER INFORMATION: Synthetic Oligonucleotide

<400> SEQUENCE: 46
gatcggaaga gcacacgtct gaactccagt cacgccaata tctcgtatgc cgtcttctgc        60
ttg                                                                      63

<210> SEQ ID NO 47
<211> LENGTH: 53
<212> TYPE: DNA
<213> ORGANISM: Artificial Sequence
<220> FEATURE:
<223> OTHER INFORMATION: Synthetic Oligonucleotide
```

-continued

<400> SEQUENCE: 47
gcgcaagaua gauuuggaau auucaagaga uauuccaaau cuaucuugcg cuu         53

<210> SEQ ID NO 48
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 48
gacaccucga uac                                                     13

<210> SEQ ID NO 49
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 49
ccacgauaug                                                         10

<210> SEQ ID NO 50
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 50
auacacacuu                                                         10

<210> SEQ ID NO 51
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 51
cuagagaacg                                                         10

<210> SEQ ID NO 52
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 52
gauacgugcg c                                                       11

<210> SEQ ID NO 53
<211> LENGTH: 139
<212> TYPE: DNA
<213> ORGANISM: Artificial Sequence
<220> FEATURE:
<223> OTHER INFORMATION: Aptamers/dox conjugates -continued

```
<400> SEQUENCE: 53
ggaggacgau gcggggaagc aacacuuagu cgcgauugau acgugcgcag ucaucagacg      60
acucgcugag gauccgagac gaucgaucga ucgaucgauc gaucgaaaaa ucgaucgauc     120
gaucgaucga ucgaucgau                                                  139
```